US010441564B2

(12) United States Patent
Jia et al.

(10) Patent No.: US 10,441,564 B2
(45) Date of Patent: Oct. 15, 2019

(54) FRUCTOSE ANALOGS AND THEIR COMBINATIONS AS ANTI-CANCER AGENTS

(71) Applicants: Wei Jia, Honolulu, HI (US); Wenlian Chen, Shanghai (CN)

(72) Inventors: Wei Jia, Honolulu, HI (US); Wenlian Chen, Shanghai (CN)

(73) Assignee: Wei Jia, Honolulu, HI (US)

( * ) Notice: Subject to any disclaimer, the term of this patent is extended or adjusted under 35 U.S.C. 154(b) by 0 days.

(21) Appl. No.: 15/591,046

(22) Filed: May 9, 2017

(65) Prior Publication Data

US 2018/0133192 A1 May 17, 2018

Related U.S. Application Data

(60) Provisional application No. 62/321,671, filed on Apr. 12, 2016.

(51) Int. Cl.

| | |
|---|---|
| ***A61K 31/341*** | (2006.01) |
| ***A61K 31/7068*** | (2006.01) |
| ***A61K 9/08*** | (2006.01) |
| ***A61K 9/00*** | (2006.01) |

(52) U.S. Cl.

CPC .......... *A61K 31/341* (2013.01); *A61K 9/0019* (2013.01); *A61K 9/0053* (2013.01); *A61K 31/7068* (2013.01); *A61K 9/08* (2013.01)

(58) Field of Classification Search

None

See application file for complete search history.

(56) References Cited

FOREIGN PATENT DOCUMENTS

WO WO-2009025781 A1 * 2/2009 ............. A61K 45/06

OTHER PUBLICATIONS

Chen, Cancer Cell 30, 779-791, Nov. 14, 2016.*
Dills, Biochemical Archives, vol. 8, pp. 221-223, 1992.*
Lewis, Cancer Cell International 2013, 13:5.*
Use of Anthracyclines to Treat Breast Cancer has Gone Down, internet article published Sep. 14, 2012, https://www.breastcancer.org/research-news/20120914.*

* cited by examiner

*Primary Examiner* — Layla D Berry
(74) *Attorney, Agent, or Firm* — Nathaniel K Fedde; Hawaii Patent Services

(57) ABSTRACT

The present invention provides a fructose analogue and a composition thereof which can be used for cancer treatment, has a targeting effect and has little effect on normal cells, particularly when used in the treatment of acute myeloid leukemia ('AML') and pancreatic cancer and other types of cancer having similar metabolic characteristics. In the present invention, the fructose analog is selected from the group consisting of 2,5-anhydro-D-mannitol and the 2,5-anhydro-D-mannitol derivative substituted at the 1-position or 6-position by an amino group, an alkyl group or an aryl group, anhydro-D-mannitol tetraacetate and 2,5-anhydroglucitol and the like. The fructose analogs of the present invention can be used to prepare and treat cancer drugs and can be prepared as injectable preparations or oral preparations. The fructose analogues of the present invention can be used in combination with conventional anticancer drugs when used in the preparation of a medicament for the treatment of cancer. The fructose analogs of the present invention can be used in combination with glucose analogues in the treatment of cancer or organ fibrosis.

3 Claims, 41 Drawing Sheets

FRUCTOSE ANALOGS AND THEIR COMBINATIONS AS ANTI-CANCER AGENTS

TECHNICAL FIELD

The present invention relates to the field of biomedicine, and relates specifically to the use of fructose analogs and the combination of fructose analogs and glucose analogs in the treatment of cancer and organ fibrosis.

BACKGROUND

It is well known that the occurrence and development of cancer involves a series of complex molecular genetic variations, including mutations, deletions, deactivations that affect genes involved in cell differentiation, regulation of cell proliferation and epigenetic modification (Ferrara, Lancet, 2013. 381 (9865): 484-95; Ghaneh, Gut, 2007. 56 (8): 1134-52). Due to the high complexity of genetic variations, the development of therapeutic drugs targeting these variations is highly challenging. Recent studies have shown that metabolic reprogramming is a hallmark of malignant tumors (Hanahan, Cell, 2011. 144 (5): 646-74.). Metabolism also plays a very important role in the development and progression of the tumor (Wang, Cell, 2014. 158 (6): 1309-23; Chen, Blood, 2014. 124 (10): 1645-54. In the network structure of the biological system, the metabolic network is located downstream of the genetic network, and much less complex than the genetic network (Chen, Cancer Cell, 2016. 30 (5): 779-791). Thus, the development of therapies specifically targeting disordered metabolic pathways of cancer cells can be less challenging and more achievable. It is known that the glycolytic pathway of malignant tumor cells are extremely active in order to support the synthesis of large amounts of precursors and ATPs required for rapid cell proliferation. As a result, the glycolytic pathway has become a hot target for the development of new anticancer drugs. Acute myeloid leukemia (AML) is a lethal blood malignancy and the most common acute leukemia affecting adults and its incidence increases with age. The treatment of AML is mainly based on cytarabine and (demethoxy) daunorubicin as chemotherapy. After a standardized treatment, the 5-year survival rate for these patients is only 30% (Chen, Blood, 2014.124 (10): 1645-54.). Pancreatic cancer is among the most deadly and aggressive of all cancers. By the time that pancreatic cancer is diagnosed, many people already have disease that has spread to distant sites in the body (about 53%). The treatment options include surgery and radiotherapy/chemotherapy. Pancreatic cancer is also relatively resistant to medical treatment, and common chemotherapeutic agents for the treatment of pancreatic cancer include 5-fluorouracil (5-FU), gemcitabine, gemcitabine, capecitabine, paclitaxel and cisplatin. The 5-year survival rate for pancreatic cancer patients is still less than 5% due to the extremely low response rate to chemotherapy (Berardi, J Gastroint Dig Syst, 2013. 3 (134): 2.). It is noteworthy that the above-mentioned chemotherapeutic drugs for AML and pancreatic cancer are non-targeted, killing normal cells while killing tumor cells, thus giving patients strong side effects, including severe bone marrow suppression, neurotoxicity and heart toxicity and so on. Therefore, the development of high efficiency and specificity new anti-cancer drugs, as well as efficient chemotherapy sensitizing agents, is the focus of many investigations.

The present invention provides a treatment which can be used for AML and pancreatic cancer and cancer having similar metabolic characteristics, and is targeted and has minimal influence on normal cells in view of the above deficiencies.

SUMMARY OF INVENTION

The present invention provides a fructose analogue useful for cancer therapy, which targets glycolytic pathway in cancer cells and has minimal impact on normal cells, particularly when used in AML and pancreatic cancer and cancer with similar metabolic characteristics. The present invention further provides a pharmaceutical composition for fructose analogs useful for cancer therapy. The present invention further provides the use of the fructose analogue for the preparation of a cancer therapeutic agent. In the present invention, the "fructose analogue" is selected from the group consisting of 2,5-anhydro-D-mannitol and the 2,5-anhydro-D-mannitol substituted at the 1-position or 6-position by amino, alkyl or arylated 2,5-anhydro-D-mannitol tetraacetate and 2,5-anhydroglucitol, and compounds having the following structural formula.

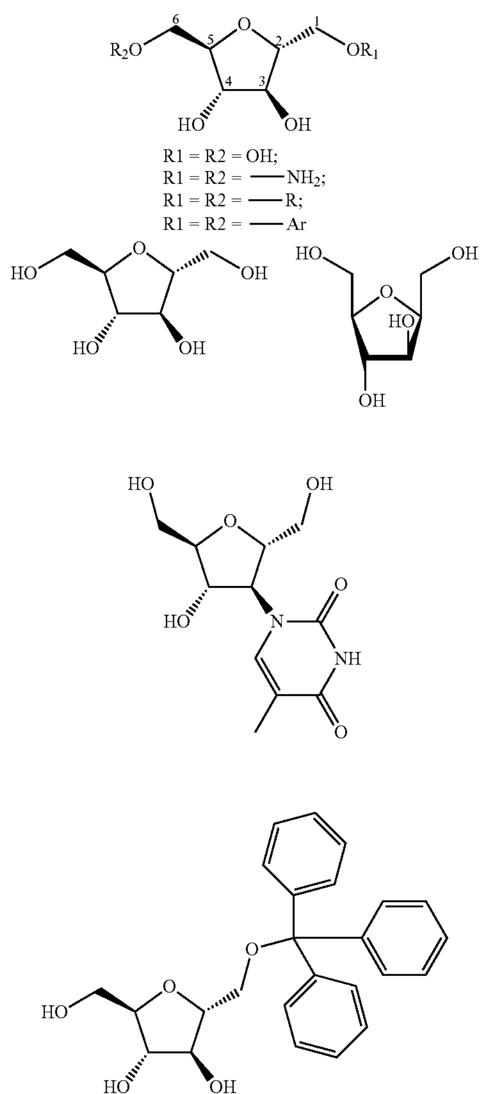

-continued
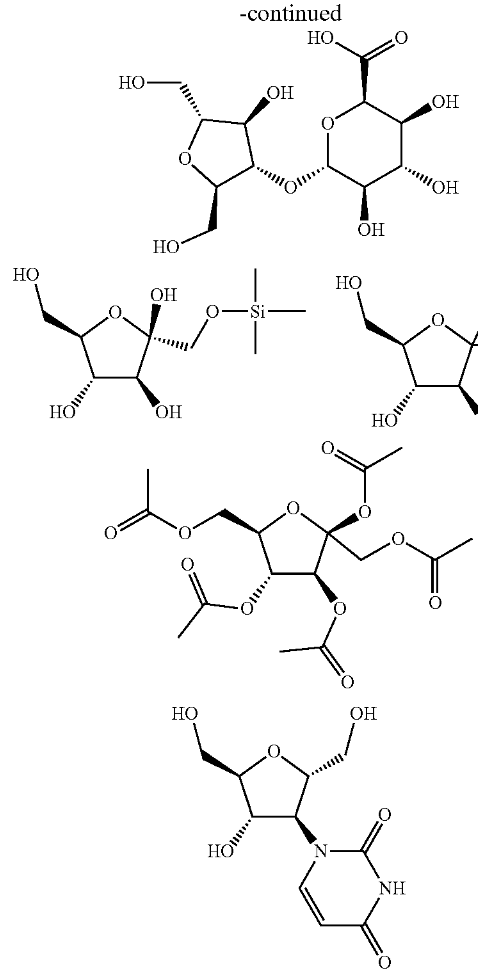
-continued
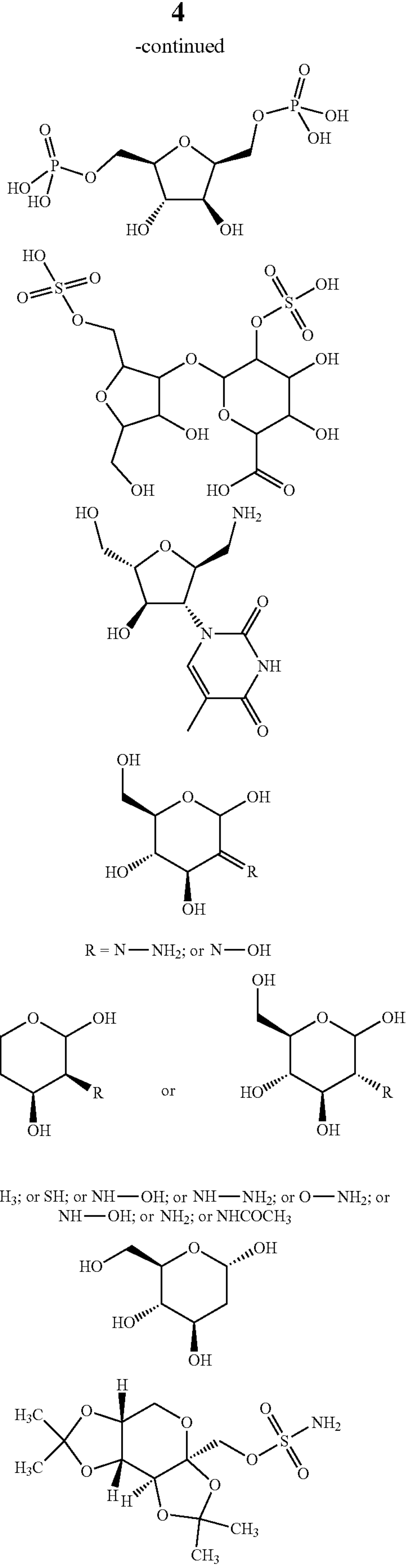

-continued

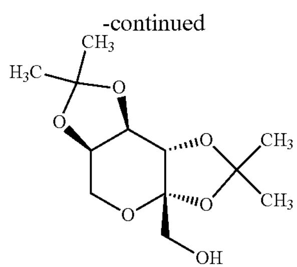

The fructose analogs of the present invention can be used for cancer treatment and can be prepared as injectable preparations or oral preparations. The cancer is selected from acute leukemia, lymphoma, melanoma, pancreatic cancer, liver cancer, esophageal cancer, gastric cancer, colorectal cancer, glioma, breast cancer, lung cancer, head and neck cancer, and kidney cancer.

In the preparation of a medicament for cancer treatment, fructose analogs can be used in combination with conventional chemotherapeutic drugs, wherein the conventional anticancer agent is selected from the group consisting of cytarabine (Ara-C), daunorubicin, doxorubicin, cisplatin, carboplatin, gemcitabine, capecitabine, sorafenib, docetaxel, paclitaxel, adriamycin, 5-fluorouracil, and so on.

The present invention also provides a composition for cancer treatment comprising one or more fructose analogs as described above, and optionally further comprising a glucose analog and a pharmaceutically acceptable excipient. The composition may be a powder or injection formulation, with a daily dose of 2,5-anhydro-D-mannitol 5-50 mg/kg patient body weight, optionally further combined with 2-deoxyglucose 5-50 mg/kg patient weight. The composition may also be an oral liquid dosage form or an oral solid dosage form with an oral daily dose of 2,5-anhydro-D-mannitol 20-200 mg/kg of patient body weight, optionally further combined with 2-deoxyglucose 20-200 Mg/kg of patient weight.

The fructose analogues of the present invention may incorporate the use of glucose analogues in the treatment of organ fibrosis, wherein the organ fibrosis is liver fibrosis, pulmonary fibrosis, renal fibrosis, myocardial fibrosis and myelofibrosis. In the present invention, the inventors have found that the above fructose analogue is useful for the treatment of cancer, comprising administering an effective amount of fructose analogue to a cancerous mammal; further comprising administering an effective dose of a fructose analogue to a cancerous mammal such as 2,5-anhydro-D-mannitol and glucose analogues such as 2-deoxyglucose); further comprising administering the fructose analogue or fructose analogue in combination with the administration of a glucose analogue for daily administration until the condition eases. The method of use includes injection or oral administration.

For this purpose, the daily dose is the injection of 2,5-anhydro-D-mannitol at 5-50 mg/kg of patient body weight, or an oral dose of 2,5-anhydro-D-mannitol at 20-200 mg/kg of patient body weight; or, an injection of a combination of 2,5-anhydro-D-mannitol at 5-50 mg/kg of patient body weight and deoxyglucose at 5-50 mg/kg of patient body weight, or an oral daily dose of 2,5-anhydro-D-mannitol at 20-200 mg/kg of body weight and 2-deoxyglucose at 20-200 mg/kg of patient body weight.

Wherein the cancer is selected from the group consisting of acute leukemia, lymphoma, melanoma, pancreatic cancer, liver cancer, esophageal cancer, gastric cancer, colorectal cancer, glioma, breast cancer, lung cancer, head and neck cancer, and kidney cancer and so on.

For use in the above applications, the treatment may be used in combination with a conventional anticancer drug selected from the group consisting of cytarabine (Ara-C), daunorubicin, doxorubicin, cisplatin, carboplatin, gemcitabine, capecitabine, sorafenib, docetaxel, paclitaxel, adriamycin, 5-fluorouracil, and so on.

The present invention also provides a composition of a pharmaceutically acceptable cancer treatment comprising one or more fructose analogs as described above, and optionally further comprising a glucose analog and a pharmaceutically acceptable excipient. The dosage form may be a powder preparation, or an injection, or an oral tablet, a capsule, or an oral solution, wherein the fructose analog is dissolved or suspended in a drinkable liquid.

The inventors have also found that the above fructose analogues in combination with the glucose analogues can be used for the treatment of organ fibrosis. The treatment includes administration of an effective amount of fructose analogs such as 2,5-anhydro-D-mannose and glucose analogues such as 2-deoxyglucose to a mammal suffering from organ fibrosis, wherein the organ fibrosis is one of the following conditions including liver fibrosis, pulmonary fibrosis, renal fibrosis, myocardial fibrosis and myelofibrosis.

E shows spleen weight measurements for normal controls, AML mice treated with vehicle, and AML mice treated with 2,5-AM; F shows WBC counts in PB for normal controls, AML mice treated with vehicle, AML mice treated with 2,5-AM, AML mice treated with Ara-C, and AML mice treated with 2,5-AM and Ara-C; G shows RBC counts in PB for normal controls, AML mice treated with vehicle, AML mice treated with 2,5-AM, AML mice treated with Ara-C, and AML mice treated with 2,5-AM and Ara-C; H shows HGB measurements in PB for normal controls, AML mice treated with vehicle, AML mice treated with 2,5-AM, AML mice treated with Ara-C, and AML mice treated with 2,5-AM and Ara-C; I shows PLT counts in PB for normal controls, AML mice treated with vehicle, AML mice treated with 2,5-AM, AML mice treated with Ara-C, and AML mice treated with 2,5-AM and Ara-C; J shows overall survival curves of AML mice treated with vehicle, AML mice treated with 2,5-AM, AML mice treated with Ara-C, and AML mice treated with 2,5-AM and Ara-C.

Figure 9A:
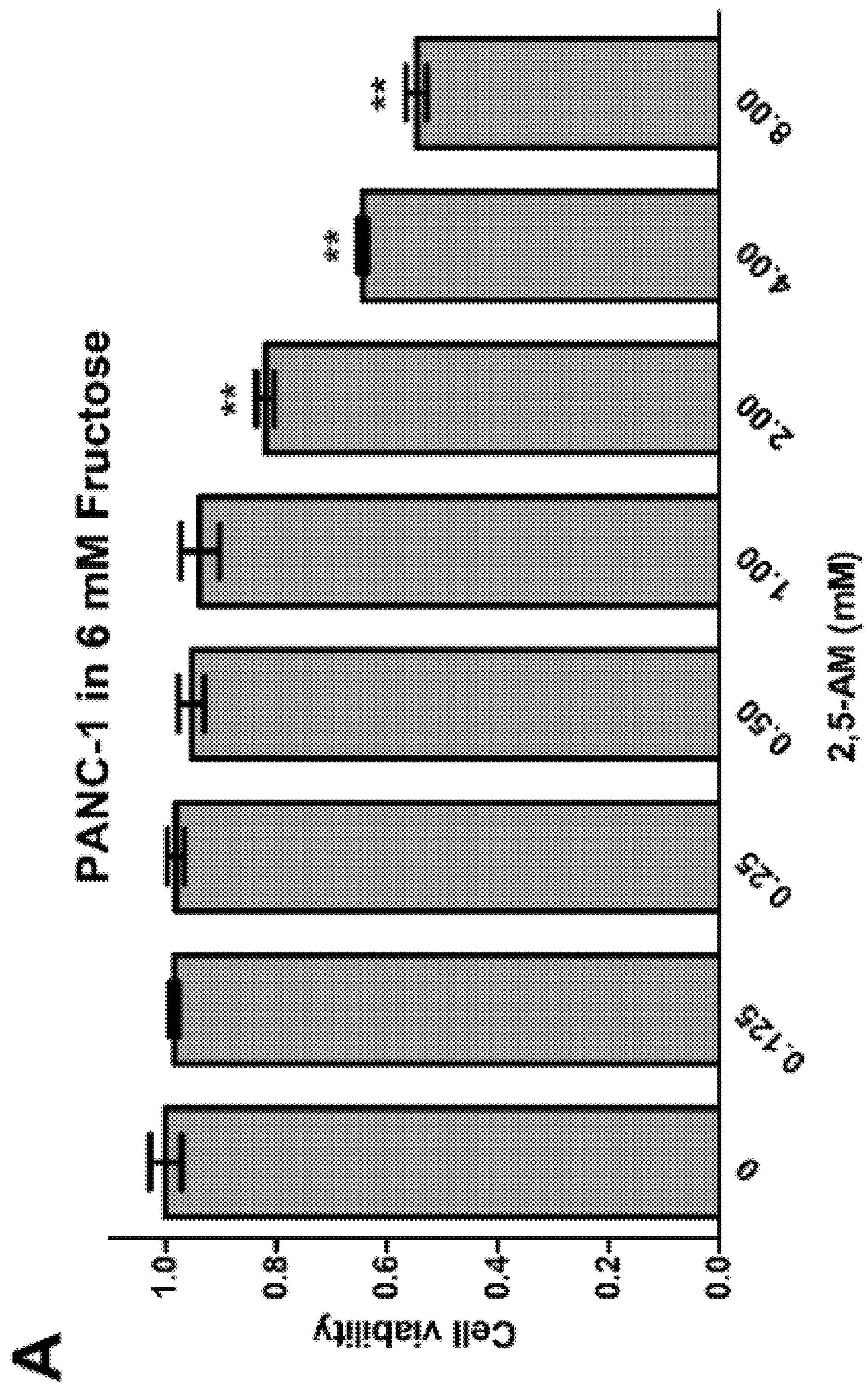
Figure 9B:
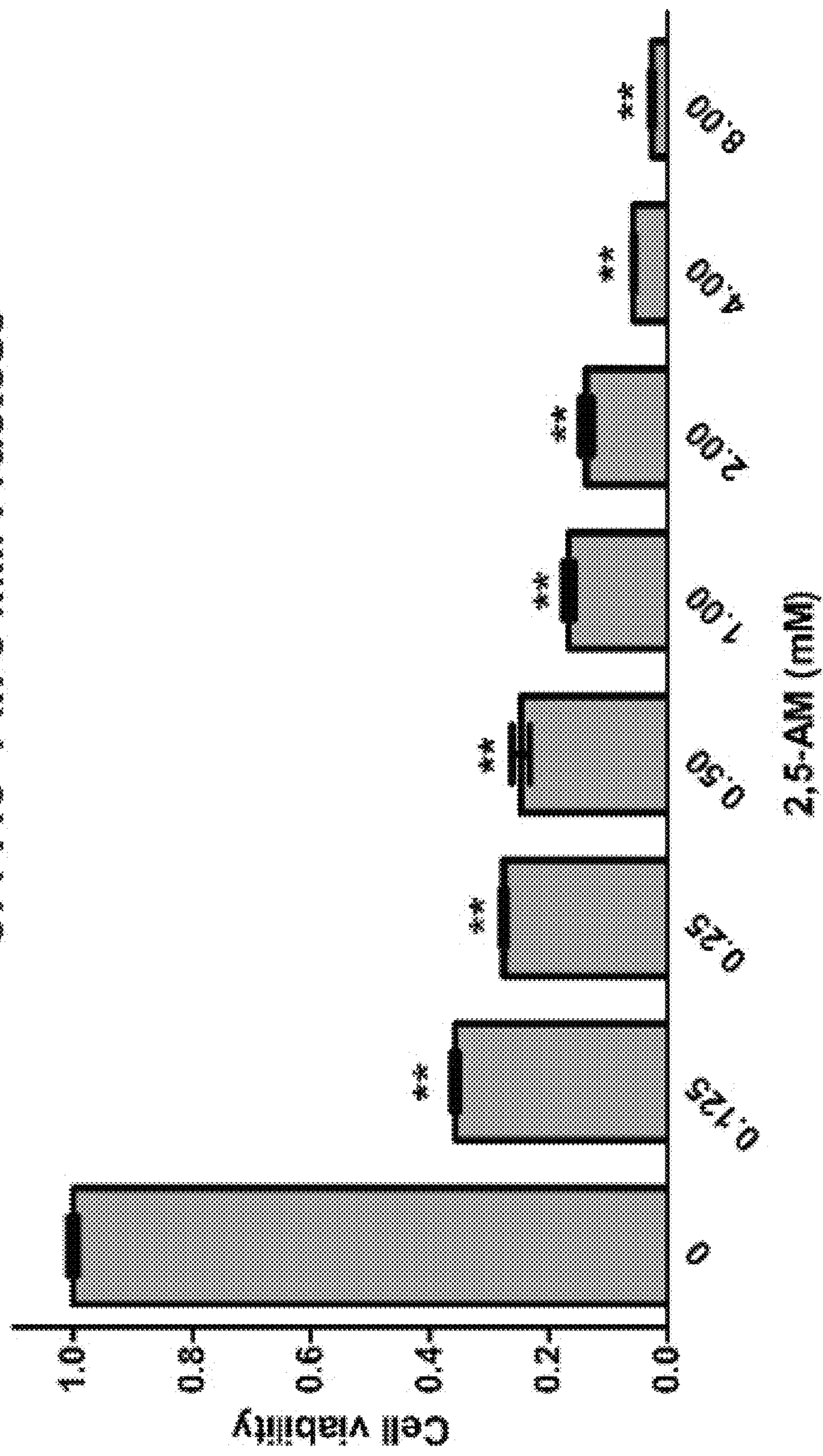
Figure 9C:
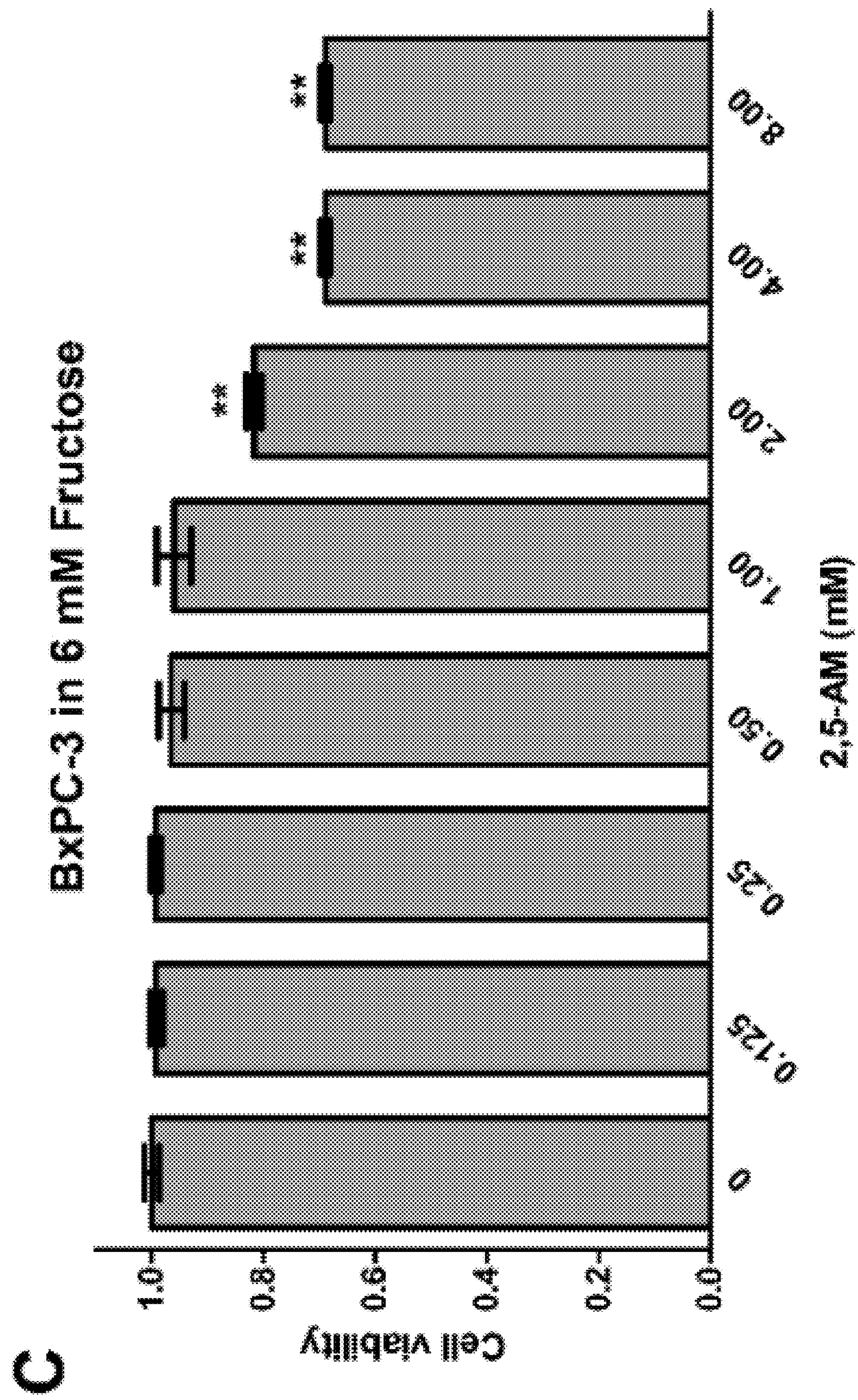

FIGS. 9A-9C. The use of 2,5-AM significantly inhibited fructose-induced proliferation of pancreatic cancer cells. Result A shows that the 2,5-AM treatment significantly inhibited the fructose-induced proliferation of pancreatic cancer PANC-1 cells; B shows that the 2,5-AM treatment significantly inhibited fructose-induced proliferation of pancreatic cancer CFPAC-1 cells; C shows that the 2,5-AM treatment significantly inhibited fructose-induced proliferation of pancreatic cancer BxPC-3 cells.

Figure 10A:
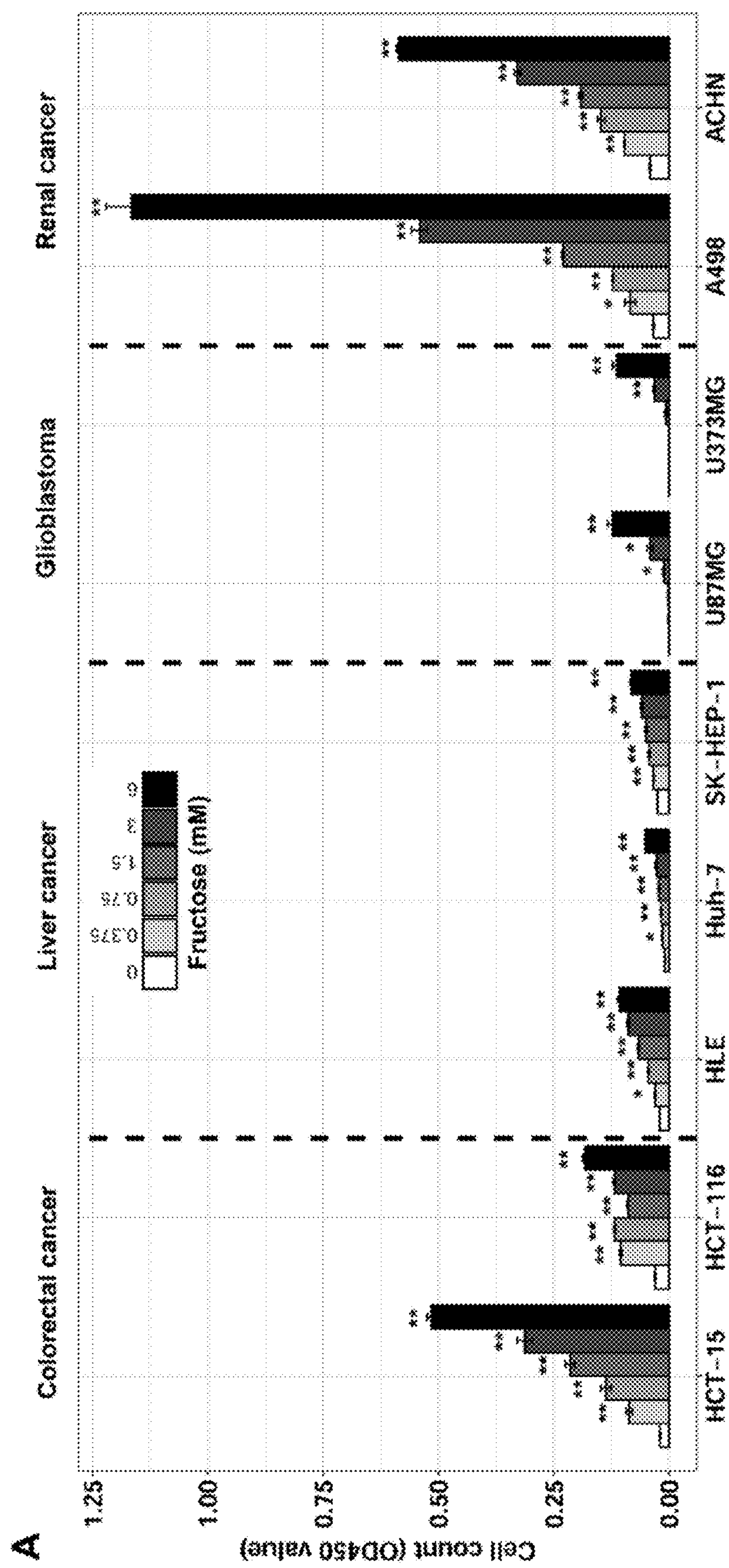
Figure 10B:
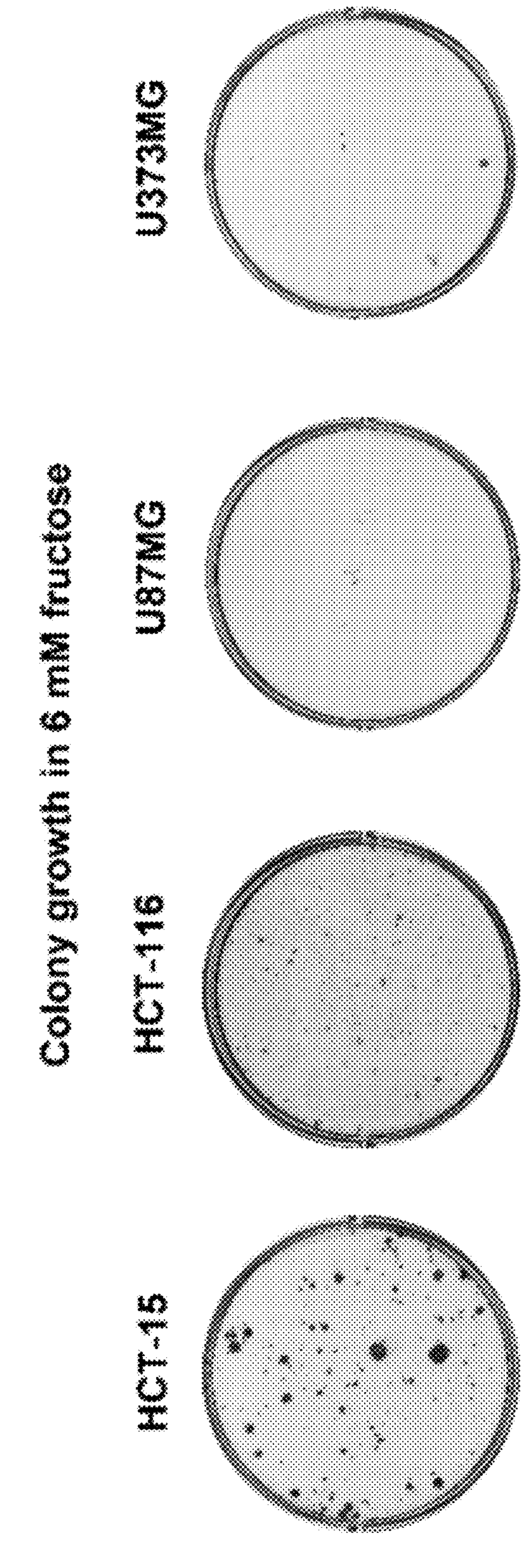
Figure 10C:
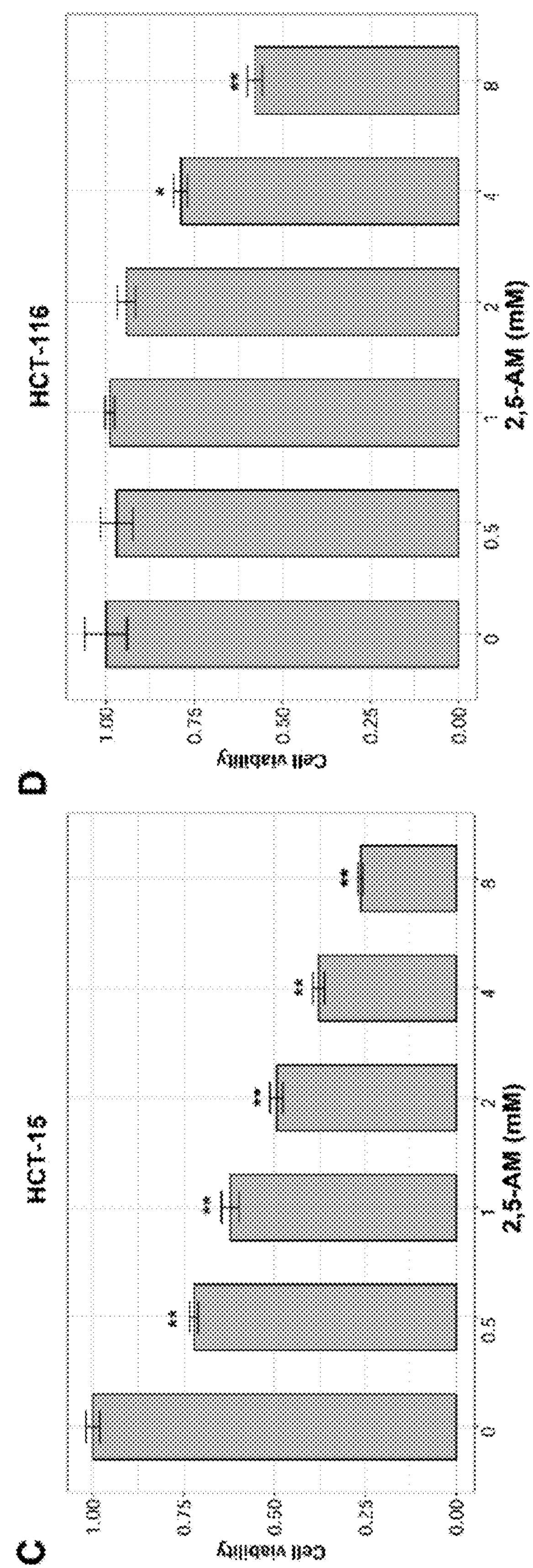

FIGS. 10A-10C Colorectal cancer cells, hepatocarcinoma cells, and glioma cells are able to utilize fructose to promote cell proliferation, and 2,5-AM treatment inhibited fructose-induced colon cancer cell proliferation. Result A shows that two colorectal cancer cell lines, three hepatocellular carcinoma cell lines, and two glioma cell lines can utilize fructose and promote the cell proliferation; B shows that colorectal cancer cells and glioma cells use fructose to promote clonal growth; C shows that 2,5-AM treatment significantly inhibited the proliferation of fructose-induced proliferation of colorectal cancer cells HCT-15; D shows that 2,5-AM treatment significantly inhibited fructose-induced proliferation of colorectal cancer cells HCT-116.

Figure 11:
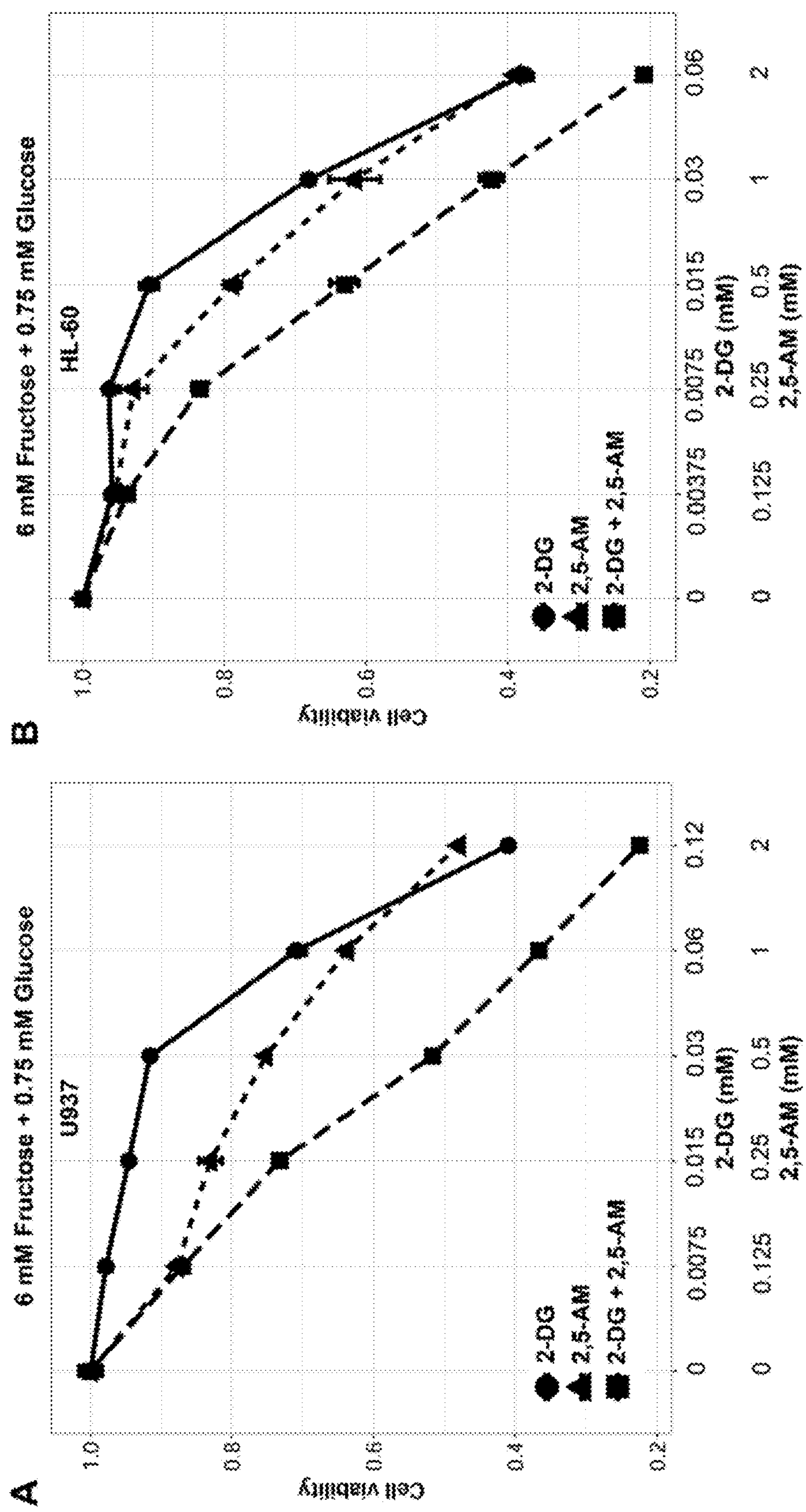

FIG. 11 2-DG and 2,5-AM synergistically inhibited AML cell proliferation. Result A shows that combination of 2-DG and 2,5-AM can kill U937 cells more effectively; B shows that combination of 2-DG and 2,5-AM can kill HL-60 cells more effectively.

DETAILED DESCRIPTION

The present inventors have discovered, for the first time, the important role of GLUTS-mediated fructose metabolism in the malignant progression of cancer, and the close relationship with the prognosis of the cancer patients, through extensive and in-depth research and clinical data analysis. Next, the present inventors have found that the fructose analogue 2,5-anhydro-D-mannitol (2,5-AM) competitively inhibits the fructose utilization by cancer cells, and that this inhibition is highly specific and has little effect on glucose utilization. The use of 2,5-AM to inhibit fructose utilization in cancer cells can significantly inhibit the fructose-induced proliferation, colonization, and migration of AML cells. Furthermore, 2,5-AM may reverse the malignant phenotypes of AML cells by synergizing with conventional chemotherapeutic cytarabine or glucose analogue 2-deoxy-glucose (2-DG). In addition, 2,5-AM inhibits fructose utilization by pancreatic cancer cells and colorectal cancer cells fructose use, and can significantly inhibit fructose-induced proliferation of the pancreatic and colorectal cancer cells. Experiments with mouse models have demonstrated that 2,5-AM can inhibit the fructose utilization by AML cells in vivo, thereby improving the leukemia phenotype of AML mice and prolonging the overall survival of mice. Moreover, 2,5-AM and cytarabine in AML mice also have a significant synergistic effect. Through the above work, the present inventors have determined the administration of 2,5-AM to AML, pancreatic cancer, and colorectal cancer, including the dosage, the route of administration and the duration of administration; and the combined use of 2,5-AM and conventional chemotherapeutic agents or 2-DG methods for cancer treatment.

Current Status and Prognosis of Acute Myeloid Leukemia and Pancreatic Cancer Treatment Acute myeloid leukemia (AML) is a group of diseases caused by abnormal hematopoietic stem cells, characterized by uncontrolled proliferation of aberrant clones of myeloid progenitor cells with impaired differentiation and by suppressed production of healthy hematopoietic cells. AML is highly heterogeneous, with an incidence of 3.8/100000. Except for the acute promyelocytic leukemia subtype (accounting for about 5% of AML), the other subtypes of AML are mainly treated with cytarabine and daunorubicin/dimethoxy daunorubicin as standardized chemotherapy regimen. AML patients after standardized treatment had a poor 5-year survival rate of about 30%. The 5-year survival rate for AML patients older than 60 years was worse, less than 10% (Sykes, Cell, 2016. 167 (1): 171-186 e15). Due to the diverse genetic and epigenetic abnormalities of individual patients, treatment efficacy and prognosis may vary significantly and there is no single treatment to cure AML patients of different molecular subtypes (Chen, Nat Genet, 2013. 45 (6): 586-7.). Therefore, there is an urgent need to develop novel and efficient targeted therapies for AML.

Pancreatic cancer is a group of pancreatic related cells that have undergone malignant transformation. The most common, pancreatic ductal adenocarcinoma, accounts for over 80% of cases. Pancreatic cancer is a high grade malignant neoplasm characterized by aggressive metastasis and infiltration, and is not sensitive to chemotherapy/radiotherapy. Thus the 5-year survival rate of pancreatic cancer patients is very low, less than 5%. About 85% of patients by the time of diagnosis has been in the advanced and unresectable stages, and thus can only choose chemotherapy as its main treatment option. Pancreatic cancer has highly complex molecular mechanisms, including oncogene mutations, tumor suppressor gene inactivation, abnormal activation of cell signaling pathway, etc., making the development of targeted therapies a huge challenge. Conventional chemotherapy for pancreatic cancer includes 5-fluorouracil (5-FU), gemcitabine, capecitabine, paclitaxel, and cisplatin.

Recent studies showed that aberrant metabolism as an important malignant feature was critically involved in the pathogenesis and progression of AML and pancreatic cancer (see Wang, Cell, 2014. 158 (6): 1309-23; Chen (5): 779-791; James, J Biol Chem, 2013. 288 (50): 36007-19; Son, Nature, & It; RTI ID=0.0 & gt; 2013. 496 (7443): 101-5.). The metabolic network is located downstream of the genetic network, involving a more limited number of core pathways that show relatively low diversity. Therefore, the development of therapeutic drugs targeting abnormal metabolic pathways is a new strategy to improve the therapeutic effect of these two diseases.

Fructose Metabolic Characteristics, Biological Significance and Clinical Significance of Acute Myeloid Leukemia and Pancreatic Carcinoma AML and pancreatic cancer have very active glycolytic metabolic profiles based on previous reports and analysis of the findings of the inventors. Previous studies by the inventors have found that active glycolytic metabolism of AML cells consumes a large amount of glucose in the bone marrow microenvironment, resulting in insufficient glucose supply. At this point, AML cells will increase the expression of fructose transporter protein GLUTS, turning to the second largest blood sugar, fructose, in serum to maintain the continued supply of energy (FIGS. 1A-E). It is known that GLUTS is encoded by the gene SLC2A5, which is the main fructose transporter of the cell and is responsible for uptake of more than 80% of fructose in cells (see Burant, J Biol Chem, 1992. 267 (21): 14523-6; Hajduch, Diabetologia, 1998. 41 (7): 821-8.)

Figure 1A:
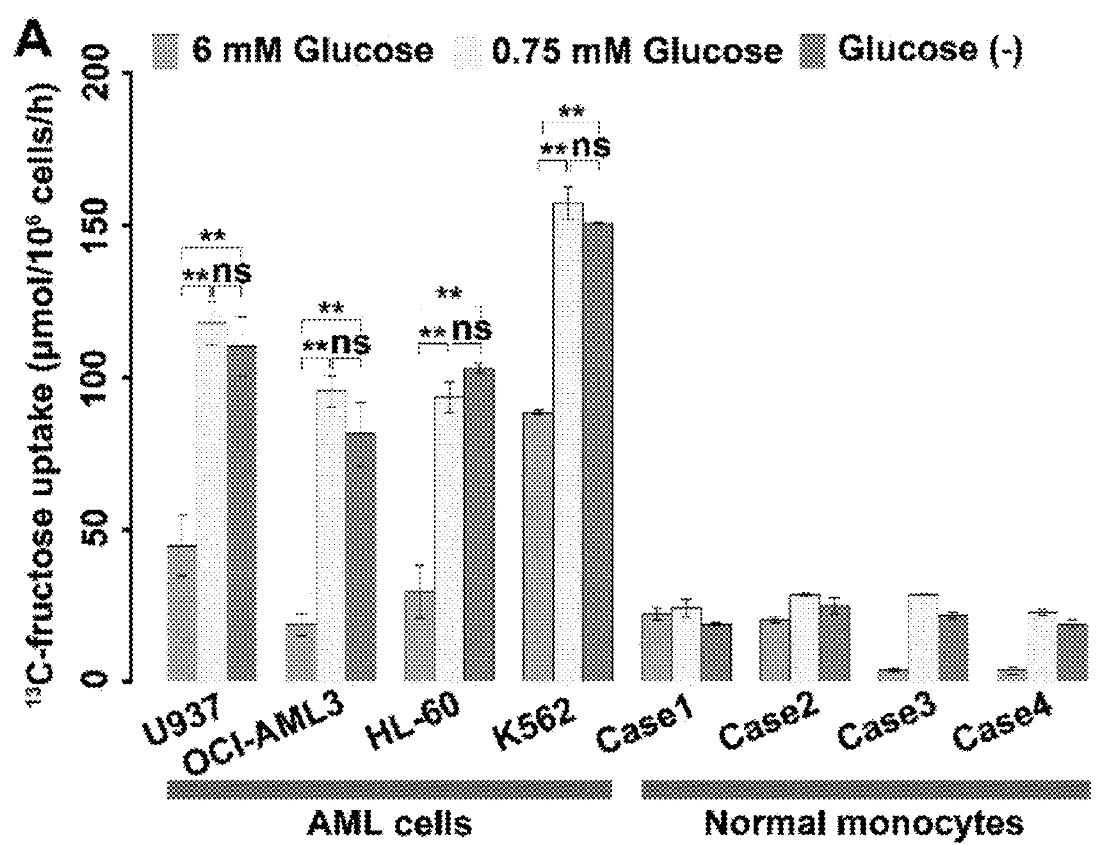
FIGS. 1A-1E The results of fructose utilization by AML cells. Where result A shows 13C-fructose uptake by AML cells and normal monocytes at different glucose concentrations; B shows Fructose-induced proliferation of AML cells and normal monocytes under the conditions of different glucose levels; C to E show that, Knockdown of AML cells significantly decreased fructose-induced cell proliferation; F shows that fructose transporter protein GLUTS was highly expressed in AML cell lines, but not in healthy monocytes. G shows that the expression of fructose transporter protein GLUTS, SLC2A5, was significantly higher in the primary AML cells from patients than in normal healthy hematopoietic cells. H shows that serum levels of fructose were significantly lower in patients with newly diagnosed AML than those of healthy controls; I shows that serum levels of fructose were significantly higher in patients with AML who achieved complete remission (CR) than serum levels of fructose at stage of initial onset.
Figure 1B:
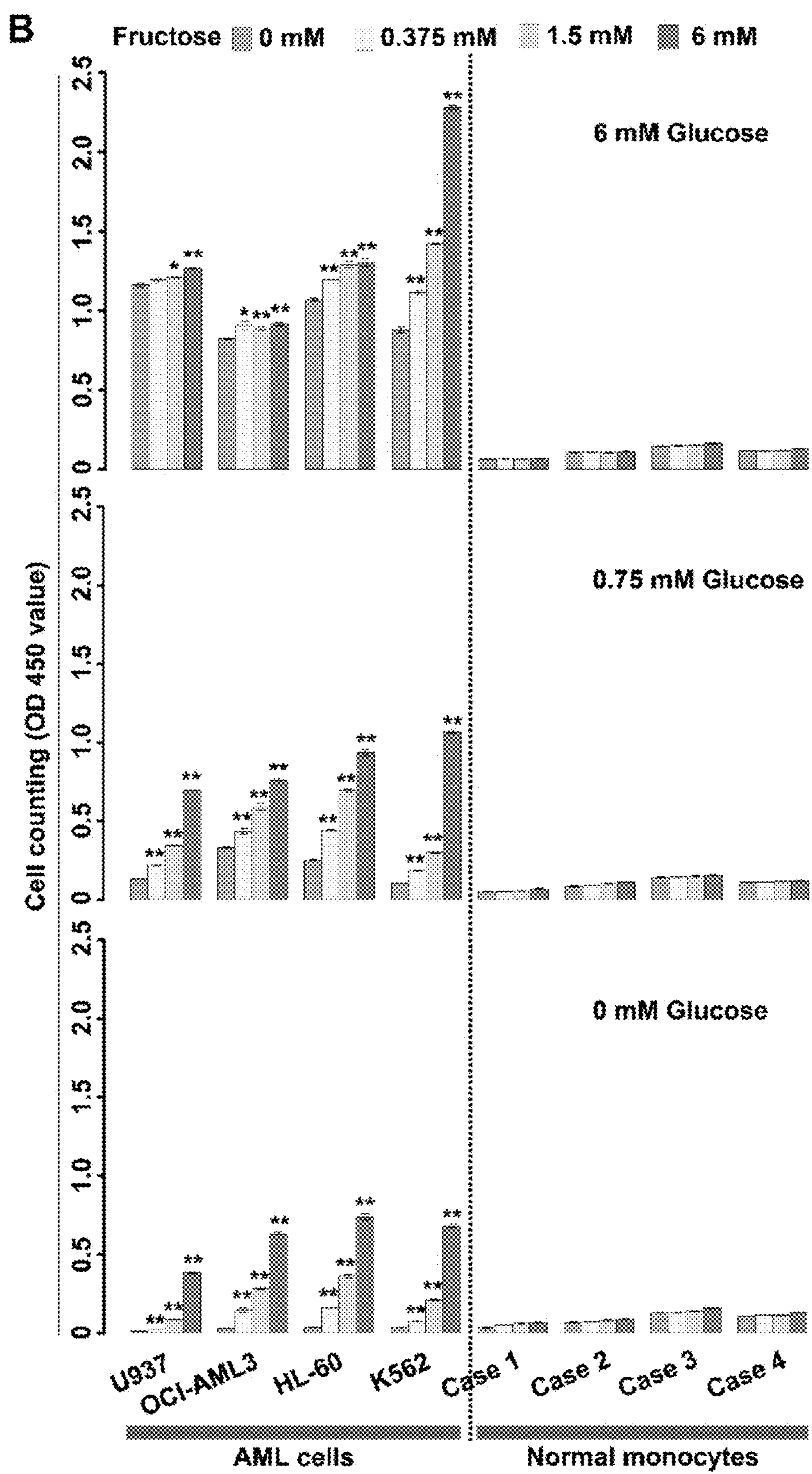
Figure 1C:
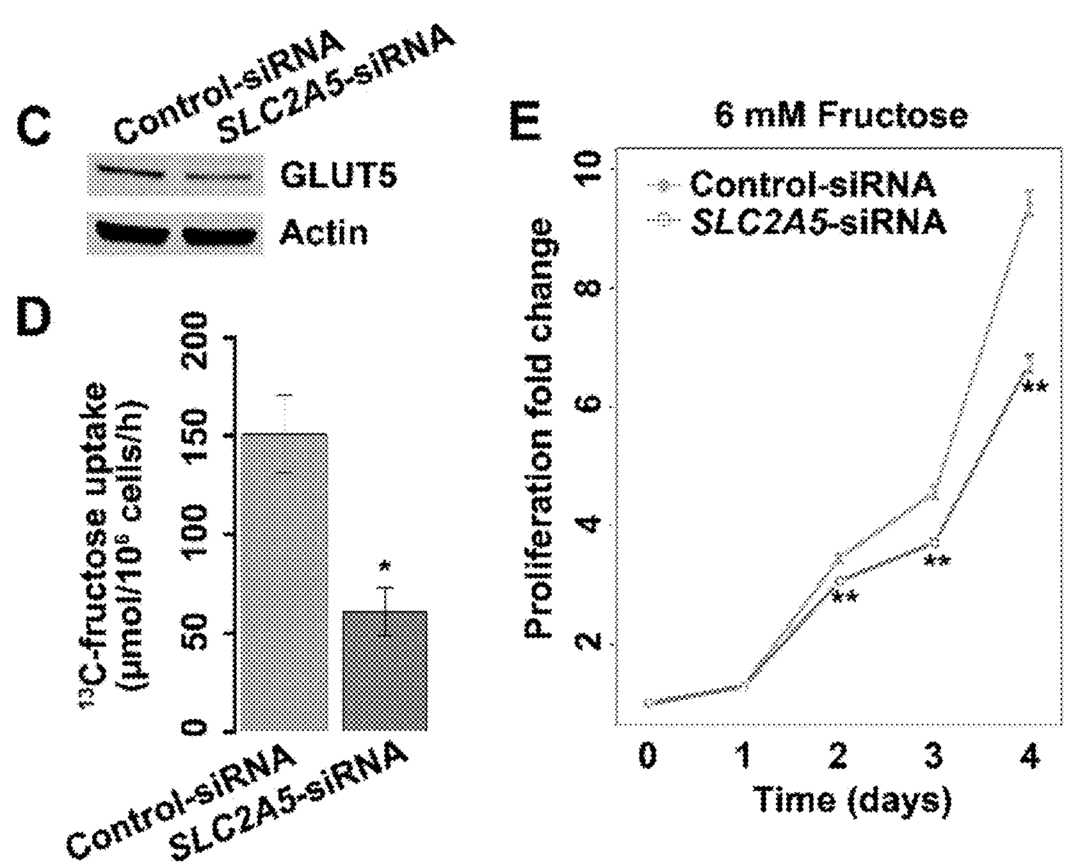
Figure 1D:
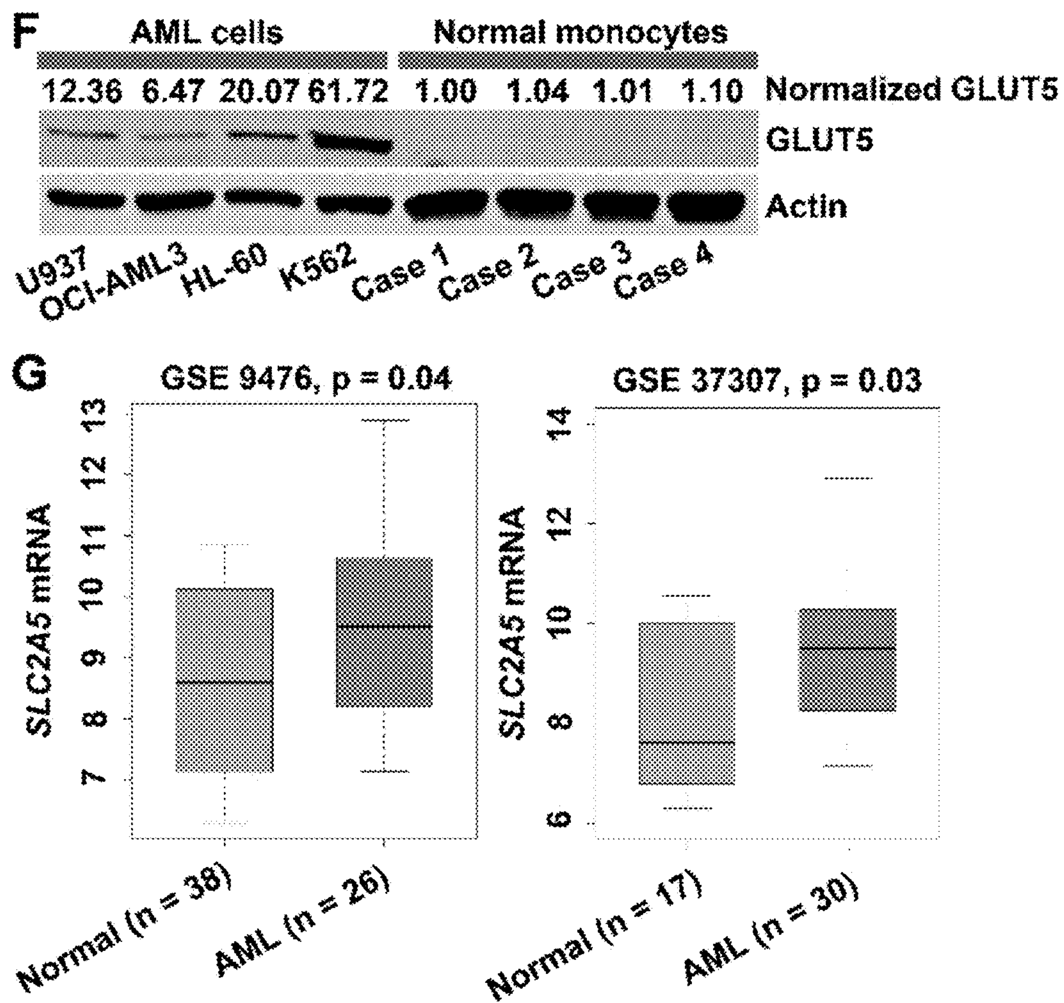
Figure 1E:
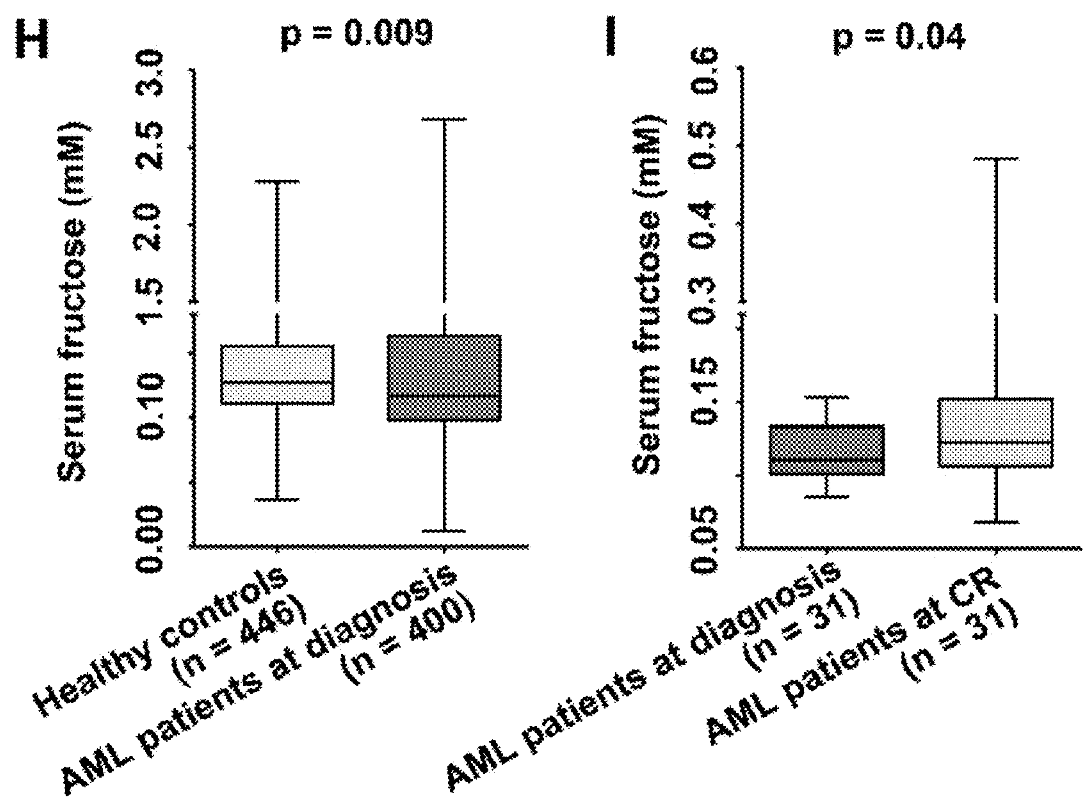
Figure 2A:
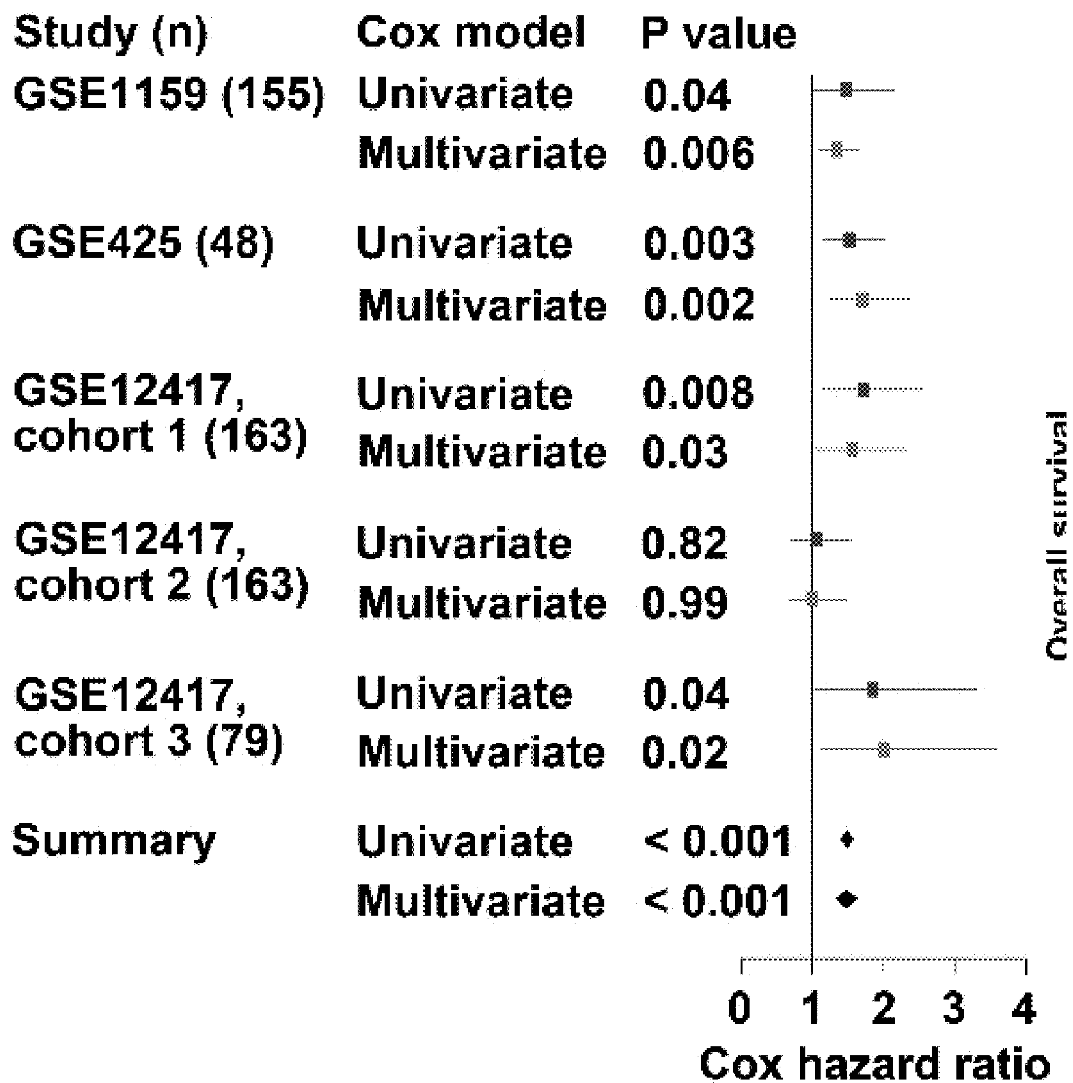
FIGS. 2A-2C The prognostic value of SLC2A5 expression levels and fructose utilization rates in AML patients. Among them, Result A shows that the higher the expression levels of SLC2A5 in bone marrow cells, the poorer survival in AML patients. B and C show that higher ability of AML patients to utilize fructose are associated with poorer response to chemotherapies.
Figure 2B:
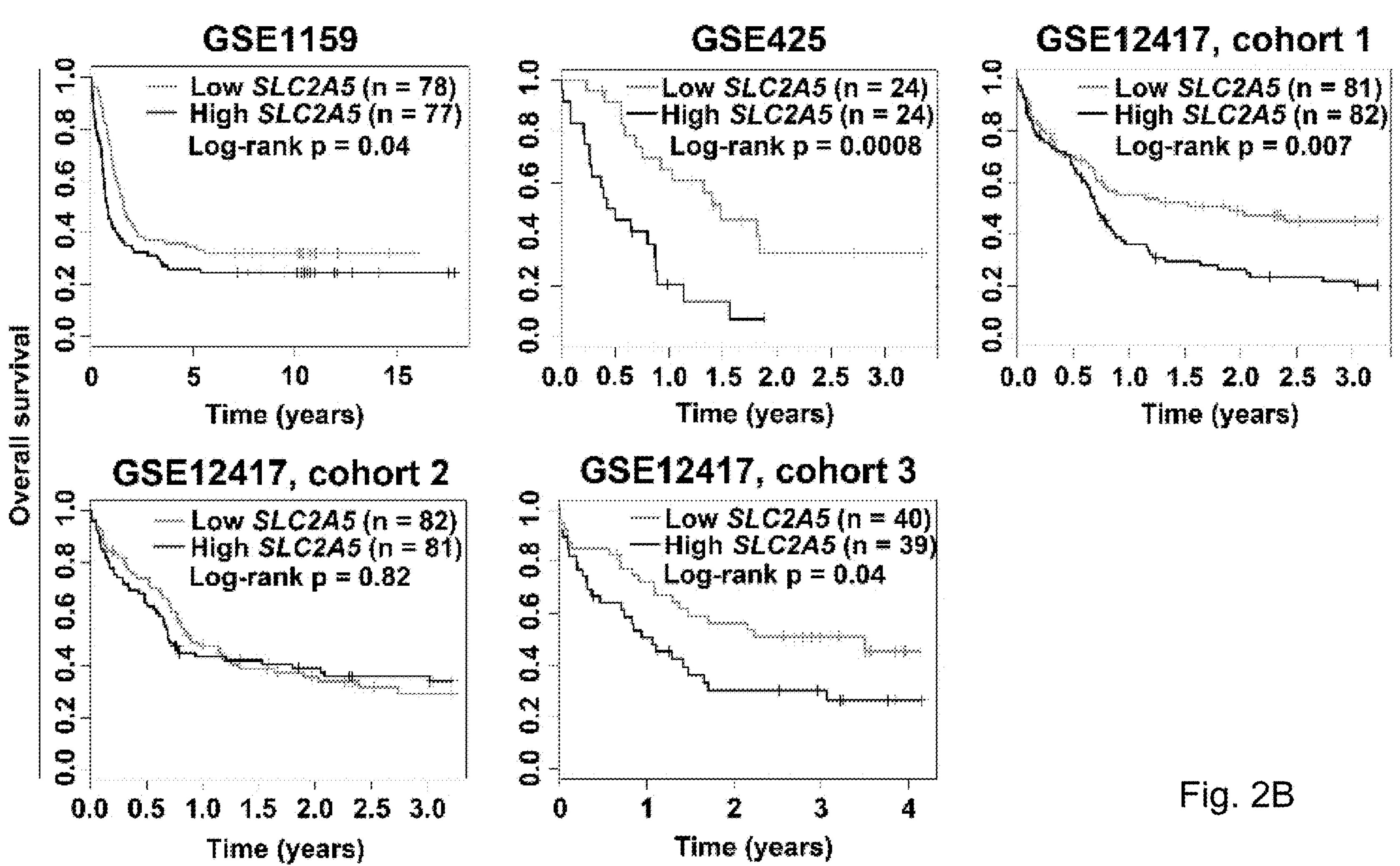
Figure 2C:
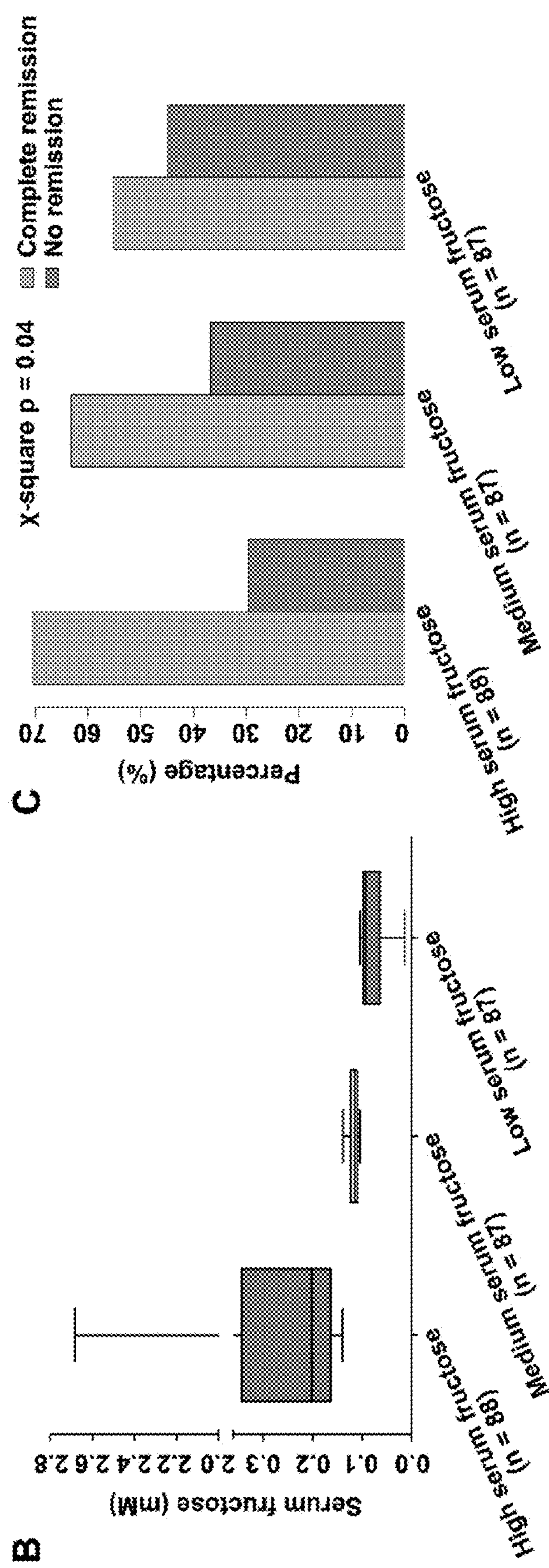
Figure 3A:
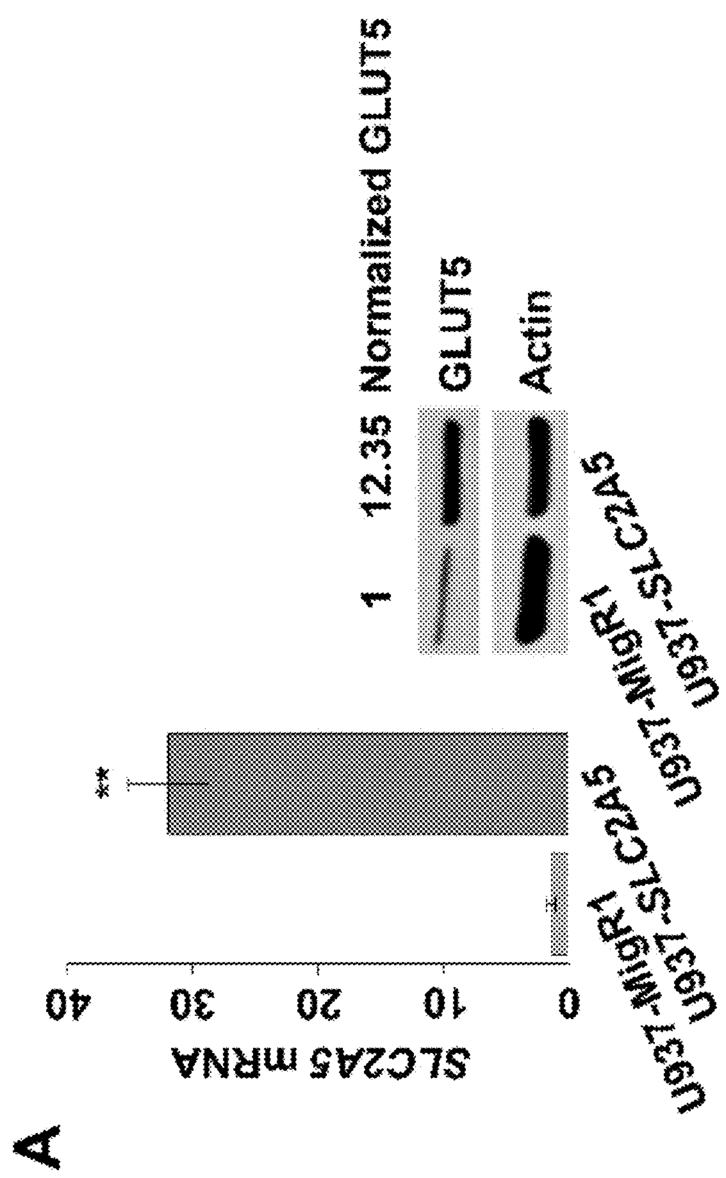
FIGS. 3A-3D Enhanced fructose utilization mediated by SLC2A5 exacerbates the leukemic phenotypes of AML cells. Result A shows the over-expression of SLC2A5 in U937 cells transfected with the control MigR1 retrovirus (U937-MigR1) or MigR1-SLC2A5 retrovirus (U937-SLC2A5); B shows that U937-SLC2A5 significantly increased fructose uptake compared to the control cell lines; C to E show that U937-SLC2A5 had a higher proliferation rate in the presence of fructose compared to the control cell lines; F to H show that U937-SLC2A5 had stronger colony formation ability in the presence of fructose compared to the control cell lines; I shows that U937-SLC2A5 had a stronger ability to migrate in the presence of fructose compared to the control cell lines; J shows that U937-SLC2A5 had higher invasive activity in the presence of fructose compared to the control cell lines FIGS. 4A-4D The expression of fructose transporter gene SLC2A5 in pancreatic cancer and its prognostic significance. Among them, result A shows that the expression of SLC2A5, the fructose transporter gene, was significantly up-regulated in pancreatic cancer tissues compared with adjacent tissues; B shows that the expression level of fructose transporter SLC2A5 was positively correlated with TNM staging of pancreatic cancer; The higher the expression level of SLC2A5, the worse the overall survival rate of pancreatic cancer patients.
Figure 3B:
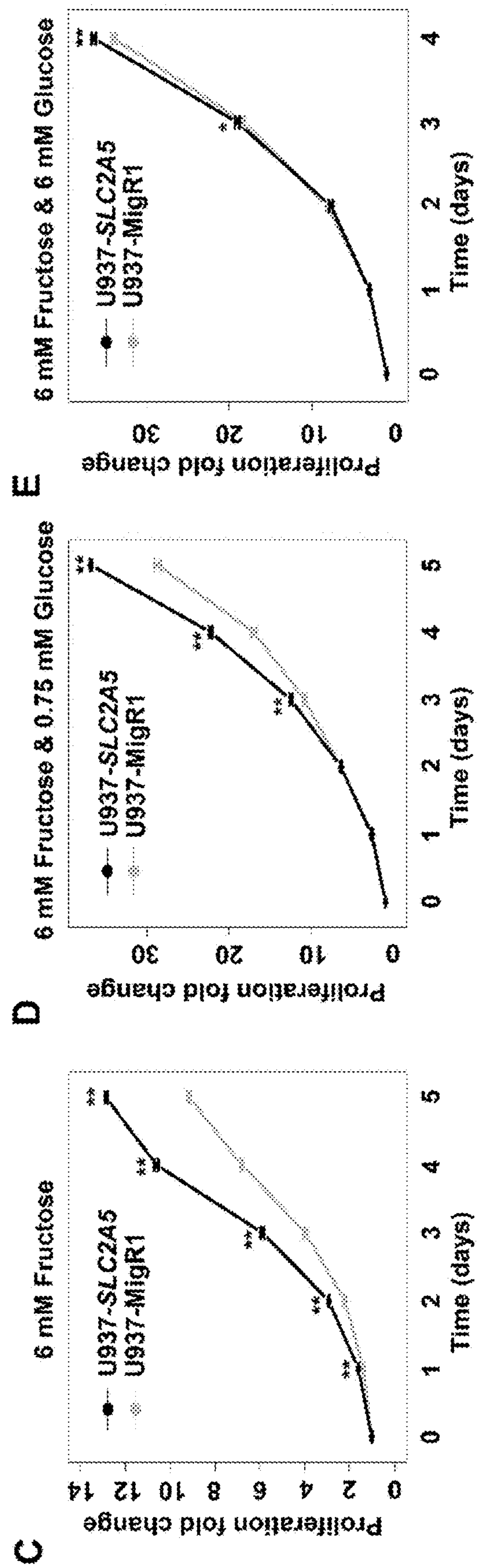
Figure 3C:
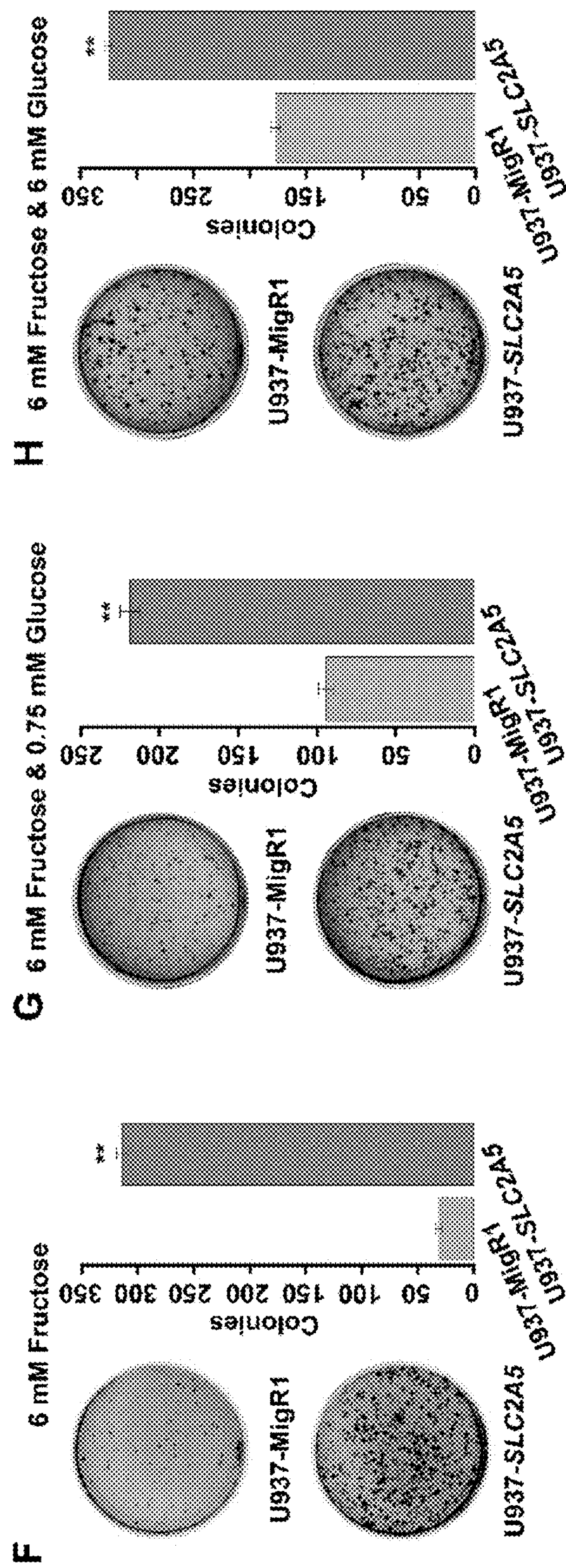
Figure 3D:
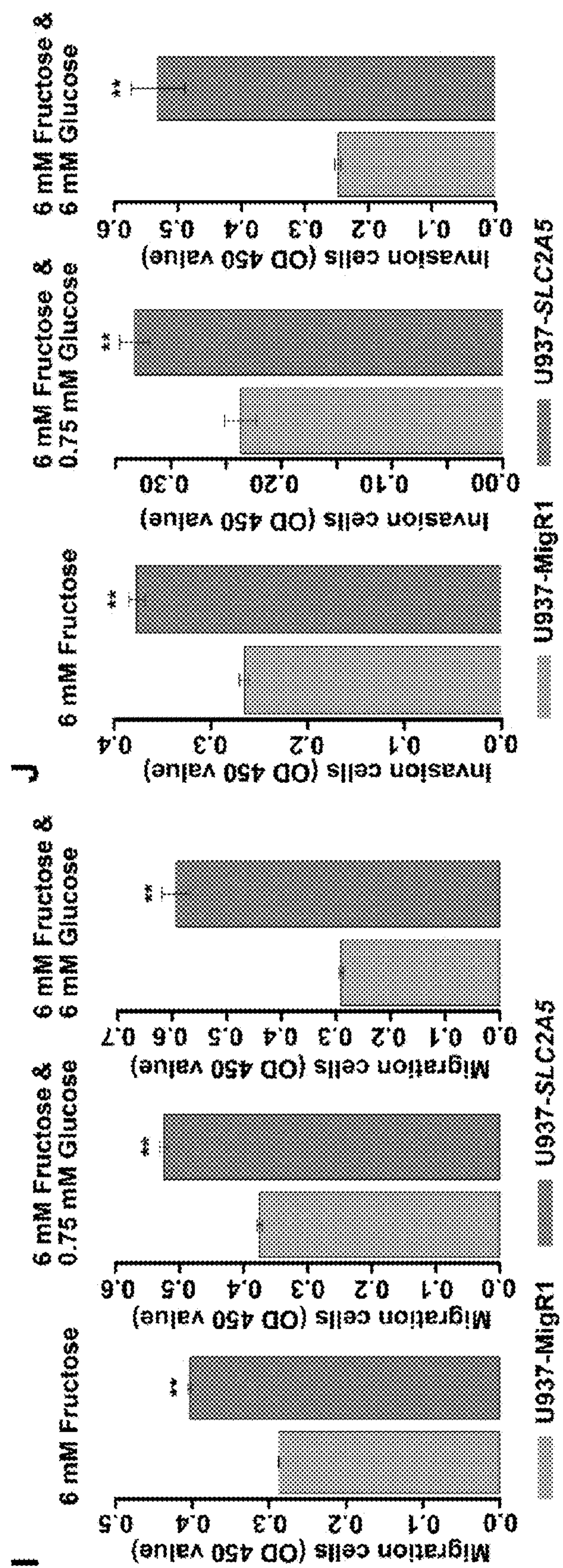
Figure 4A:
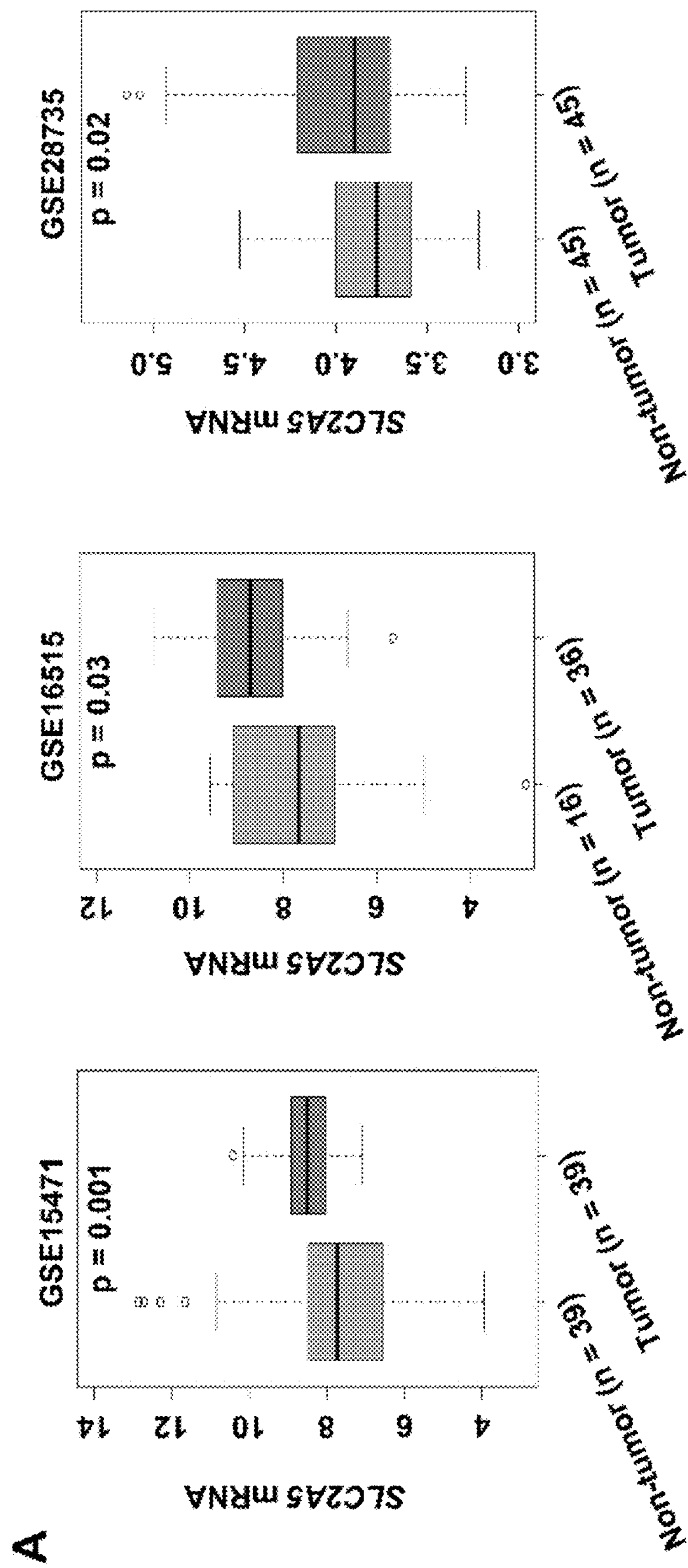
Figure 4B:
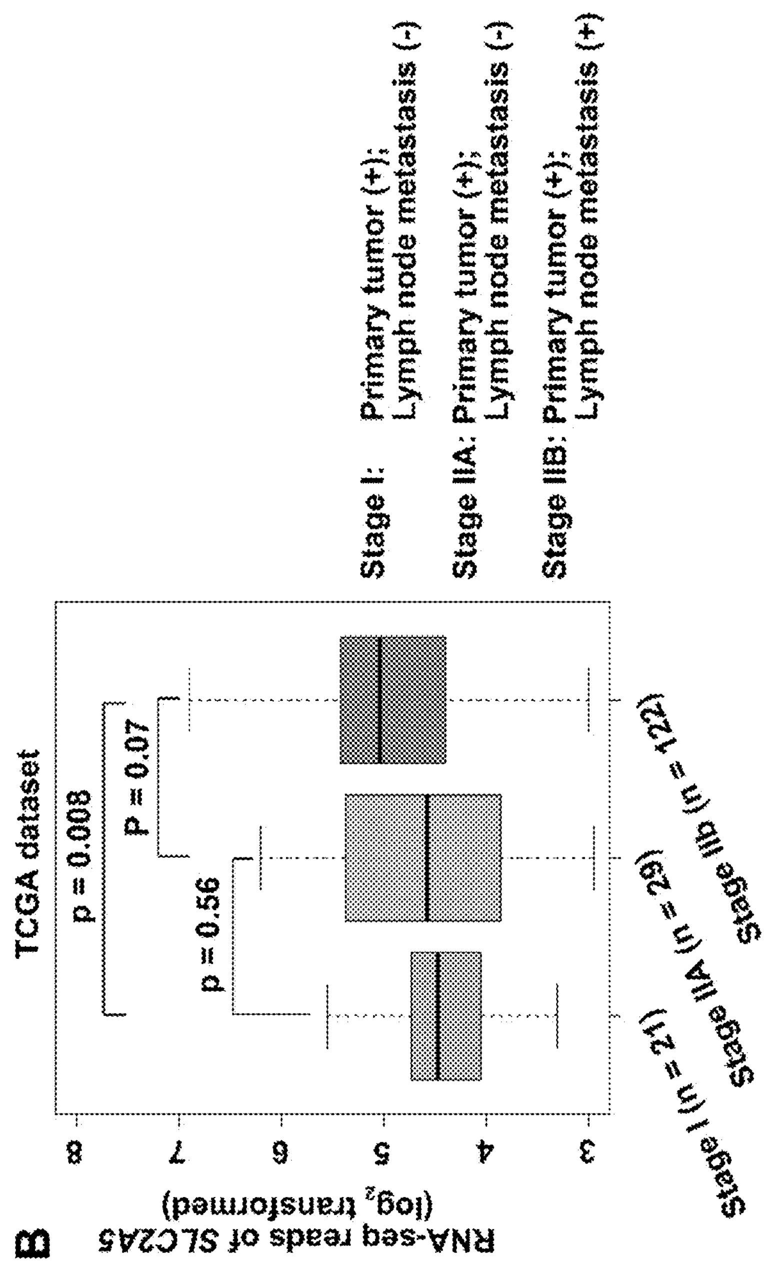
Figure 4C:
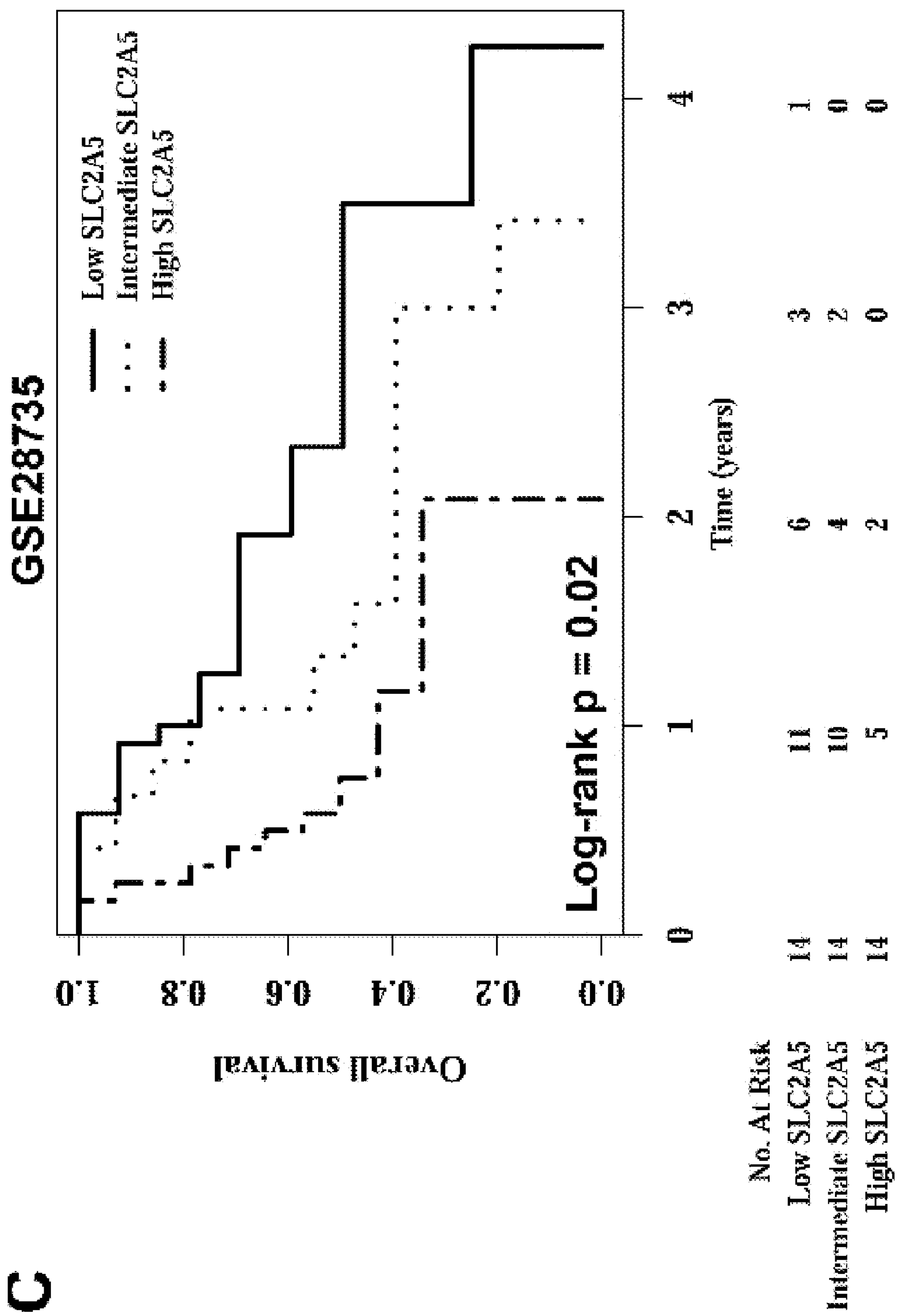
Figure 4D:
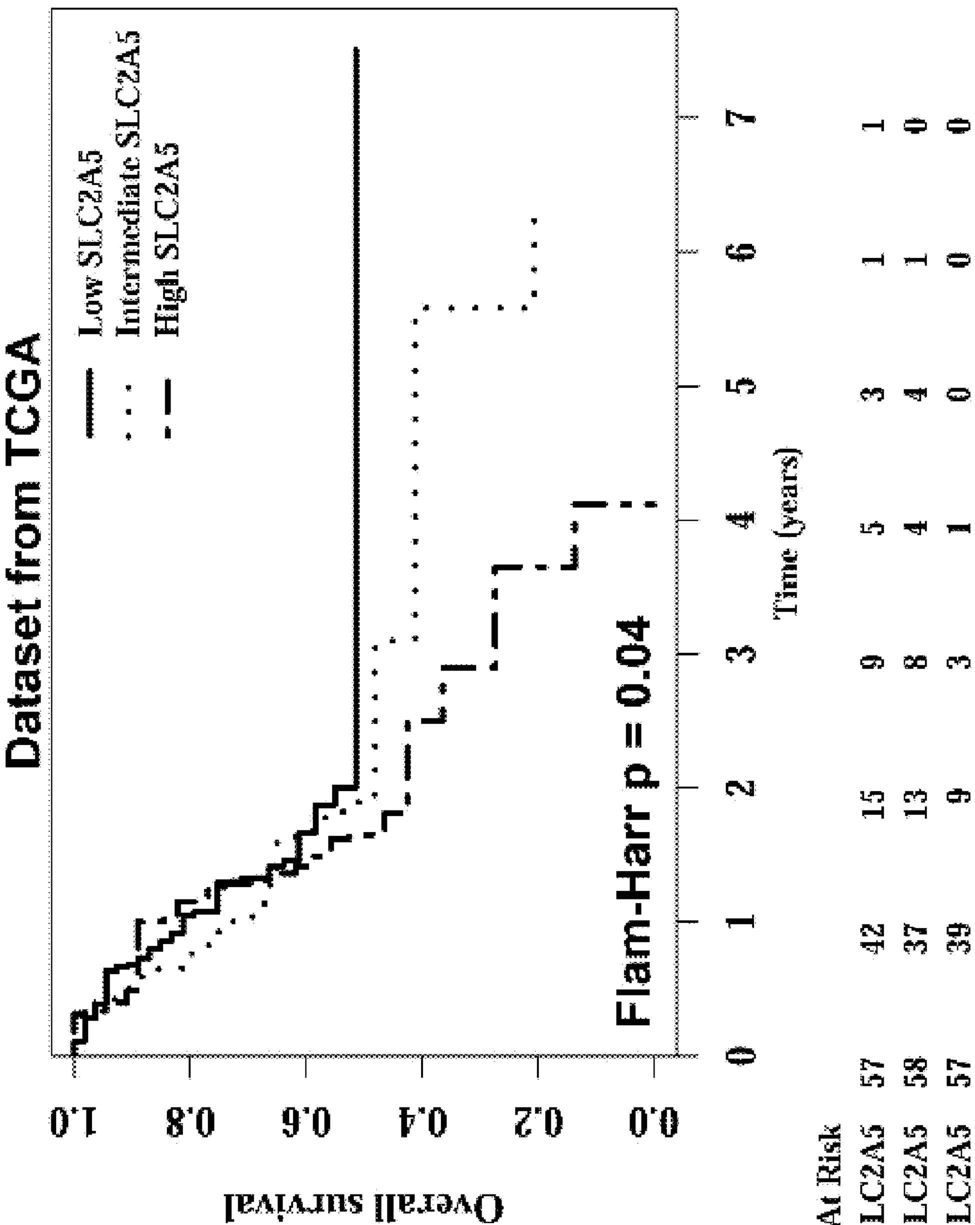
Figure 5A:
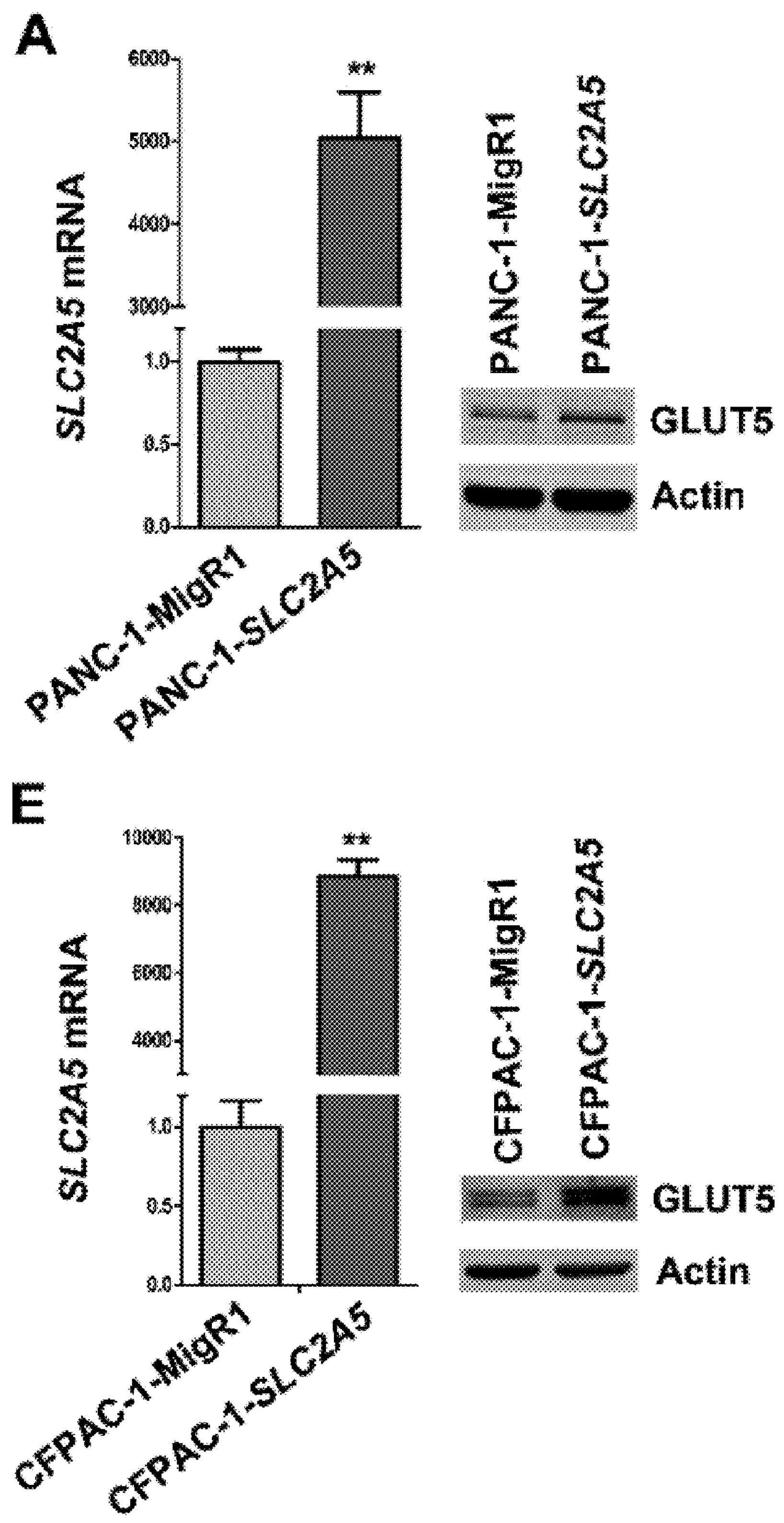
FIGS. 5A and 5B. The fructose transporter gene SLC2A5 in pancreatic cancer cells to promote fructose utilization. Result A shows the over-expression of SLC2A5 in pancreatic cancer cell PANC-1 (PANC-1-SLC2A5); C PANC-1-SLC2A5 showed enhanced proliferation rate in the presence of fructose compared to the control cell line; D shows that PANC-1-SLC2A5 is more capable of colony formation in the presence of fructose compared to the control cell lines; E shows that overexpression of SLC2A5 in pancreatic cancer cell line CFPAC-1 (CFPAC-1-SLC2A5); G shows that CFPAC-1-SLC2A5 was more proliferating in the presence of fructose compared with the control cell lines; H shows that compared with the control cell lines, CFPAC-1-SLC2A5 has stronger ability to form colonies in the presence of fructose.
Figure 5B:
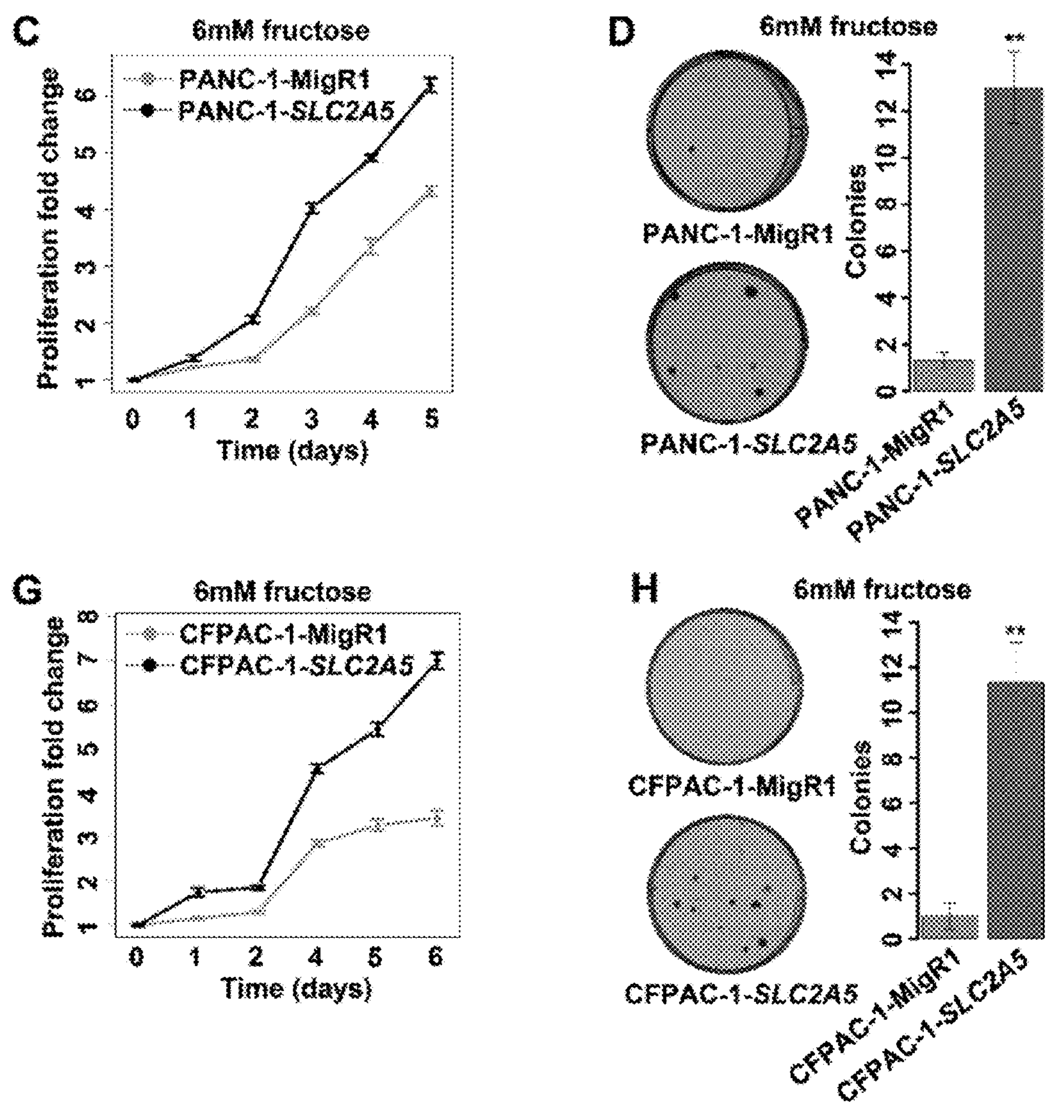
Figure 6A:
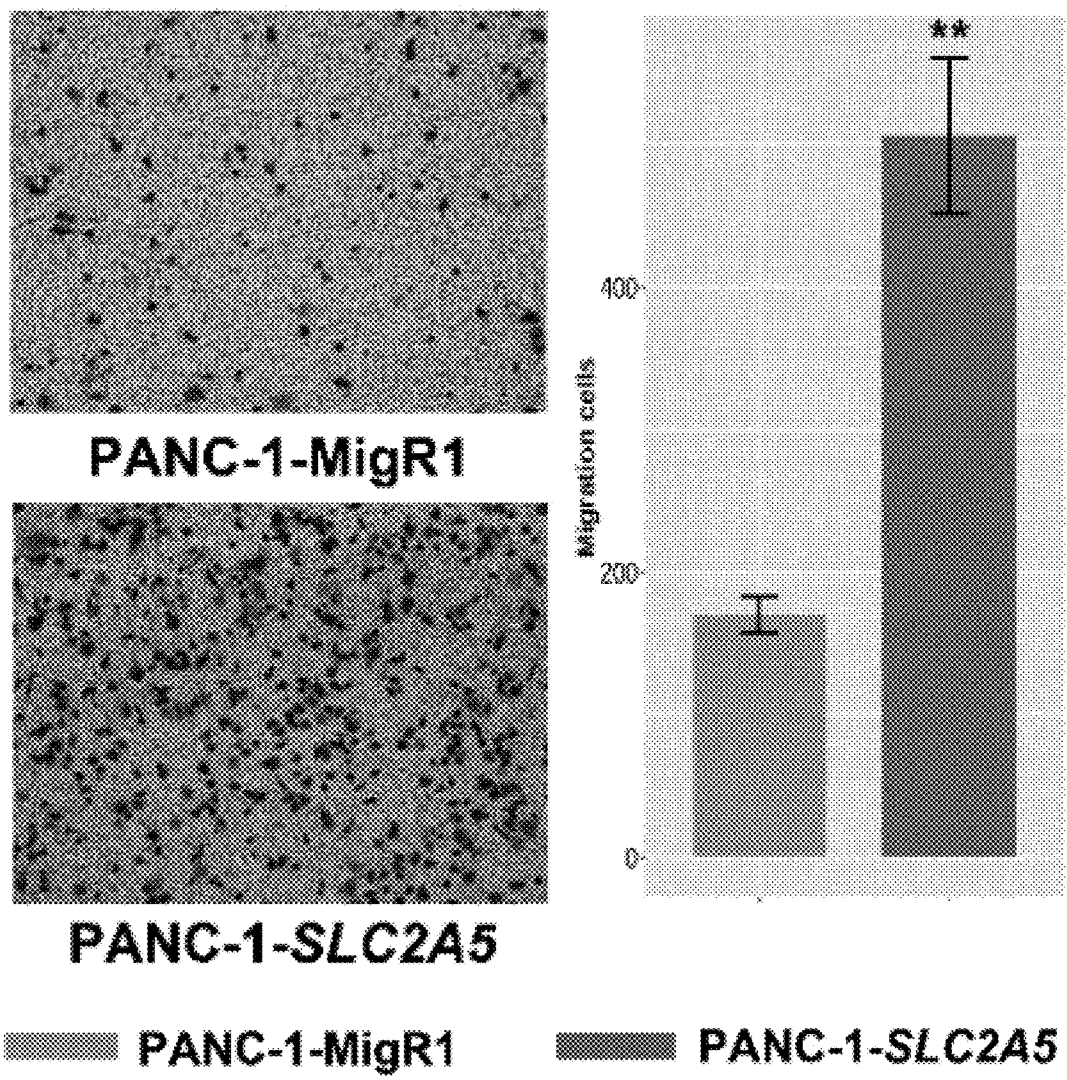
FIGS. 6A-6F. Enhanced fructose metabolism mediated by GLUT-5 significantly enhances the ability of pancreatic cancer metastasis. Result A shows that PANC-1-SLC2A5 has a stronger ability to migrate in the presence of fructose compared to the control cell line; B shows that CFPAC-1-SLC2A5 has a stronger ability to migrate in the presence of fructose.
Figure 6B:
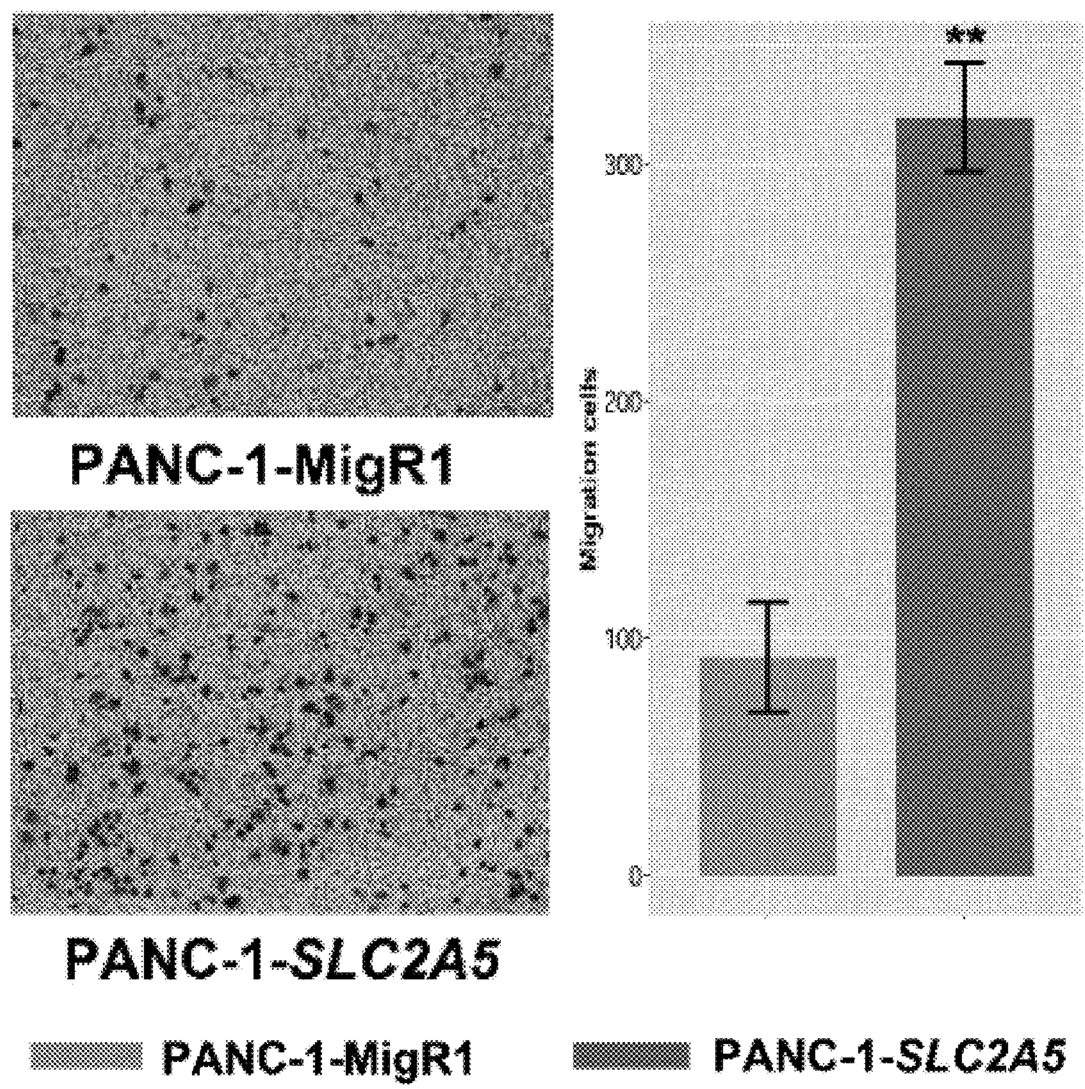
Figure 6C:
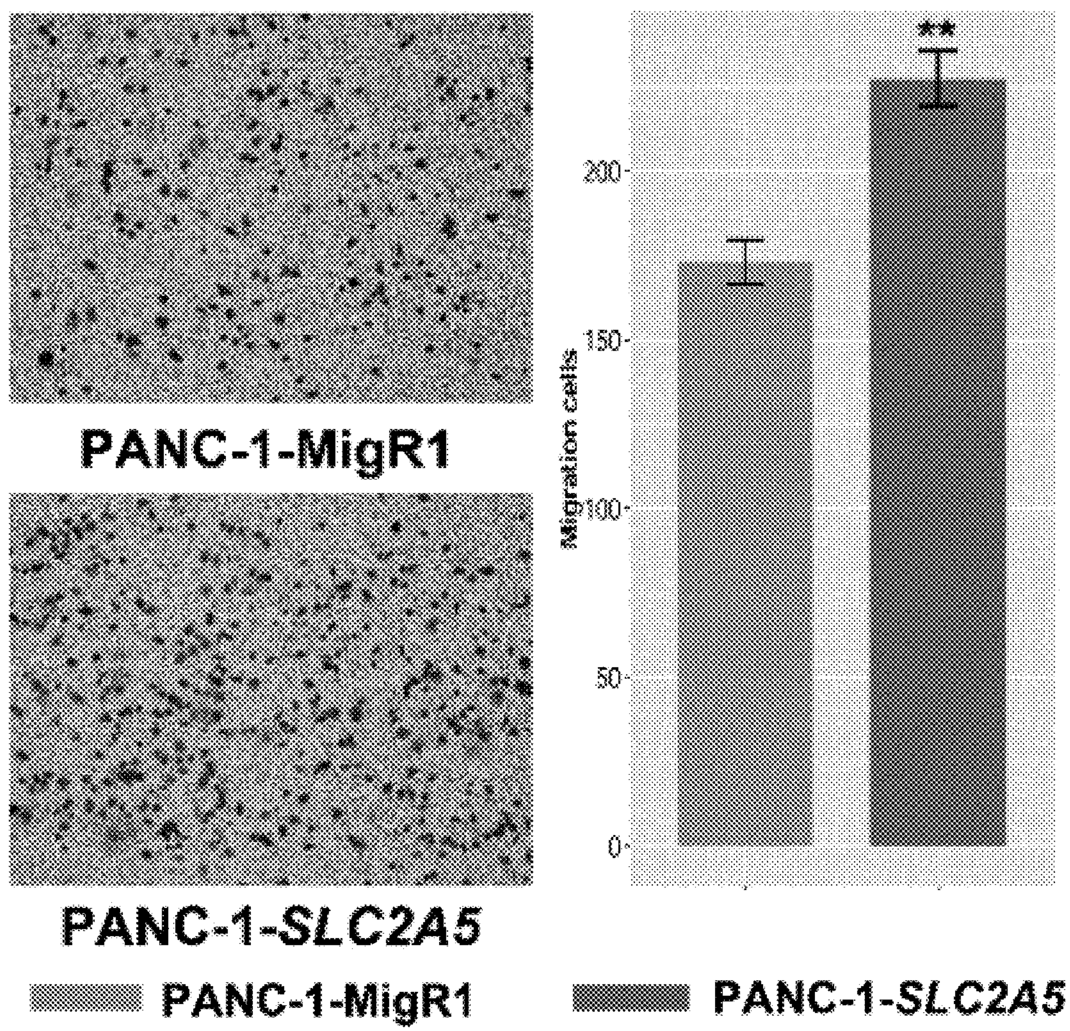
Figure 6D:
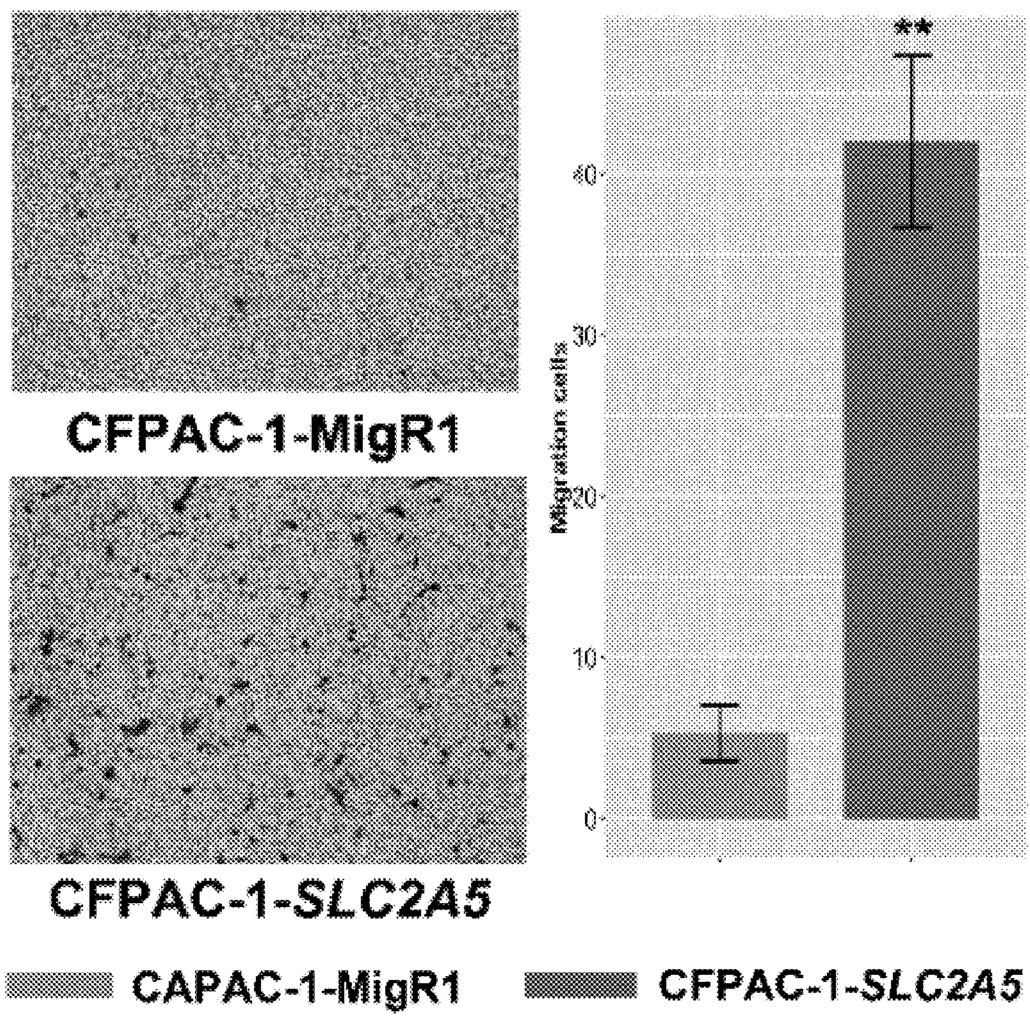
Figure 6E:
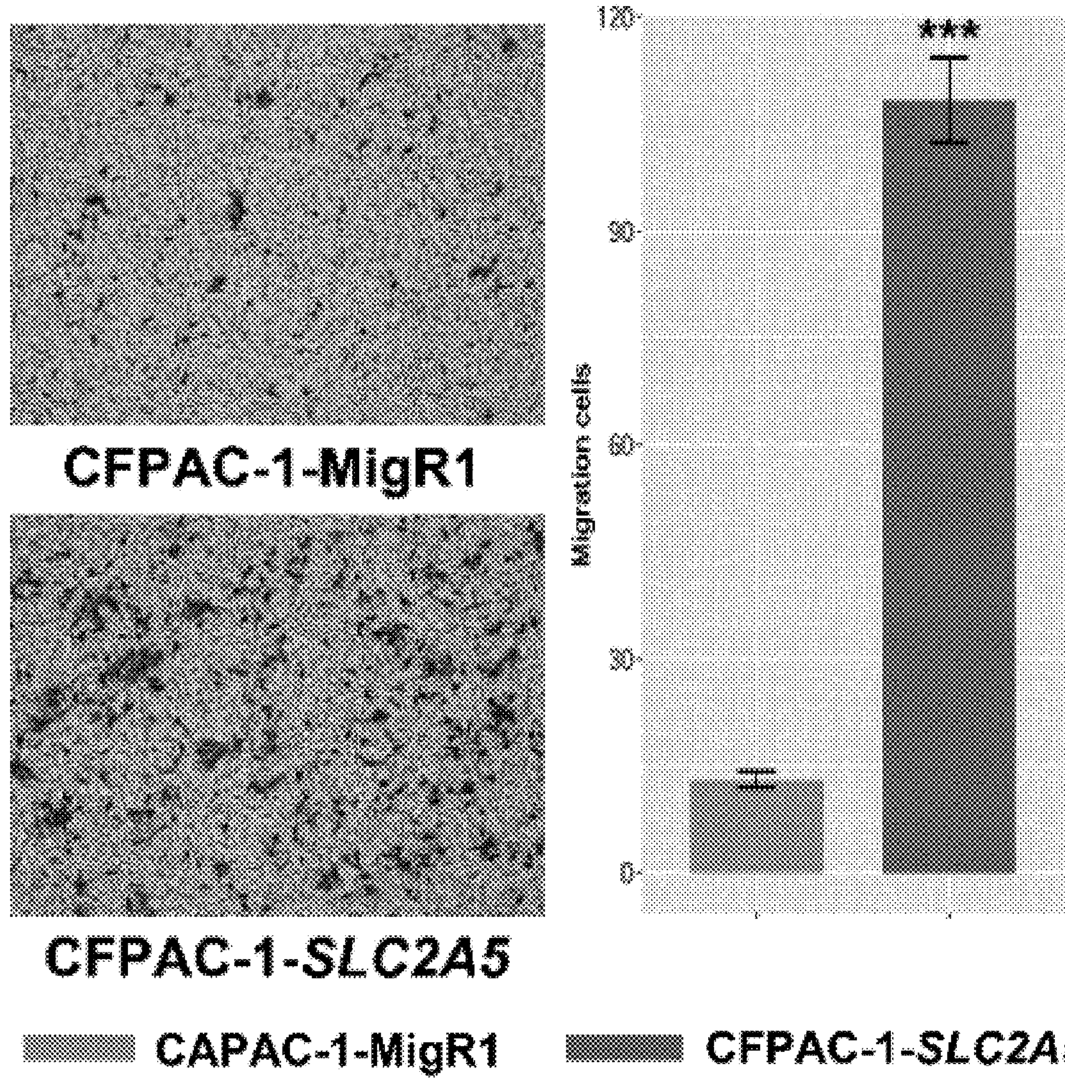
Figure 6F:
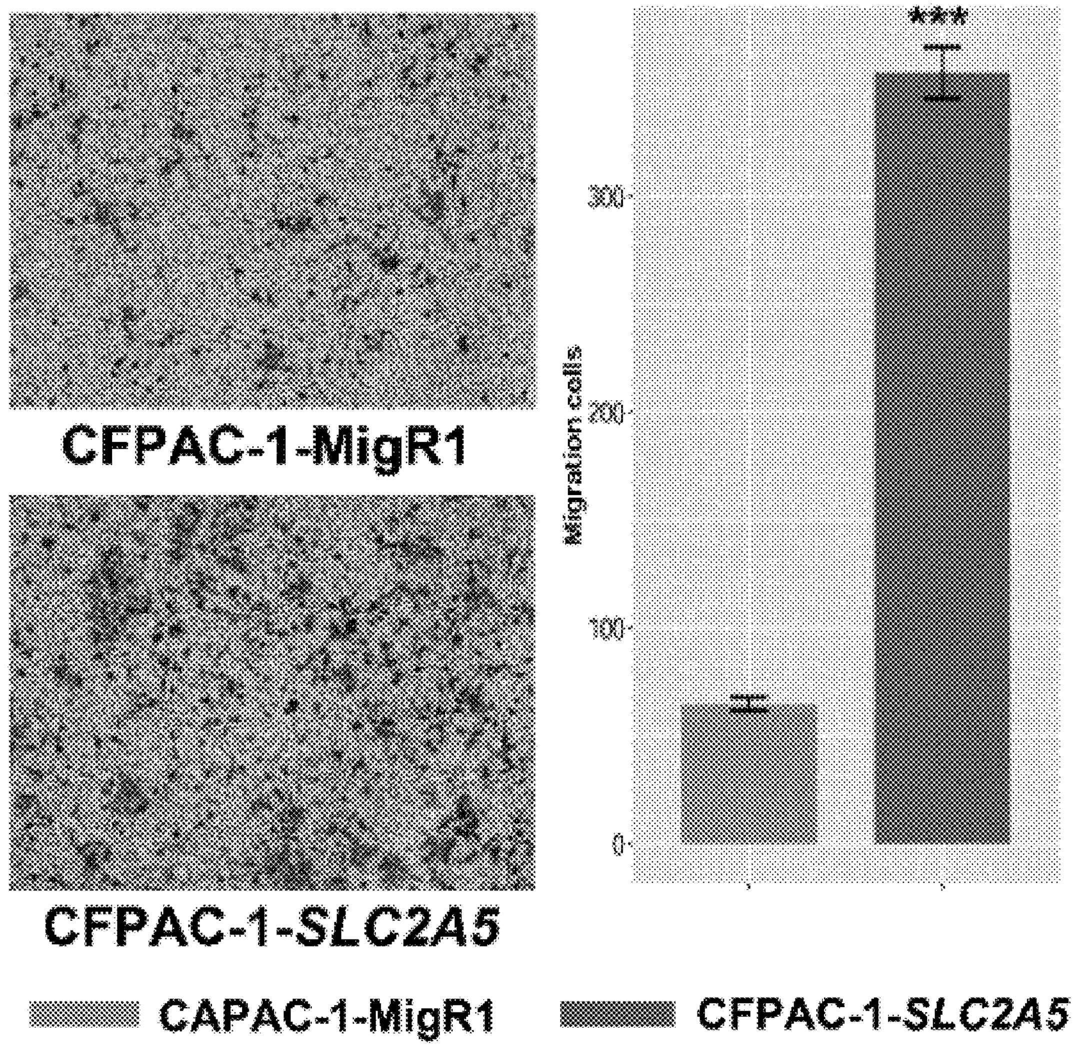
Figure 7A:
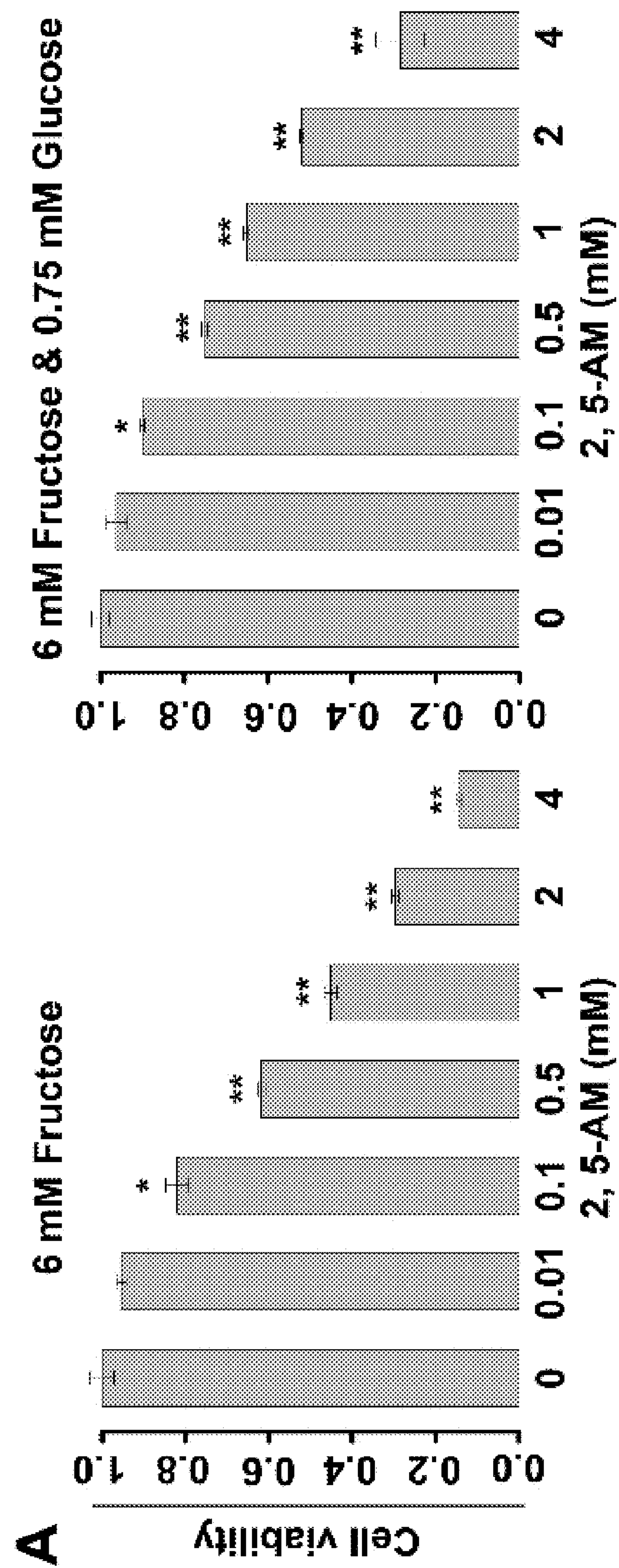
FIGS. 7A-7G. The use of 2,5-AM inhibited fructose utilization by AML cells and significantly improved the malignant phenotypes of AML cells. Result A shows that 2,5-AM significantly inhibited the proliferation of U937-SLC2A5 cells in the presence of fructose; B and C show that 2,5-AM significantly inhibited the colony formation of U937-SLC2A5 cells; D shows that 2,5-AM significantly inhibited the mobility of U937-SLC2A5 cells; E shows that 2,5-AM specifically inhibited fructose-induced proliferation of AML cells but had little effect on glucose-induced cell proliferation; F shows that in the presence of fructose alone 2,5-AM can synergistically work with chemotherapeutic agent, Ara-C, to kill AML cells; G shows that in the presence of fructose and low concentration of glucose, 2,5-AM can synergistically work with Ara-C to kell AML cells.
Figure 7B:
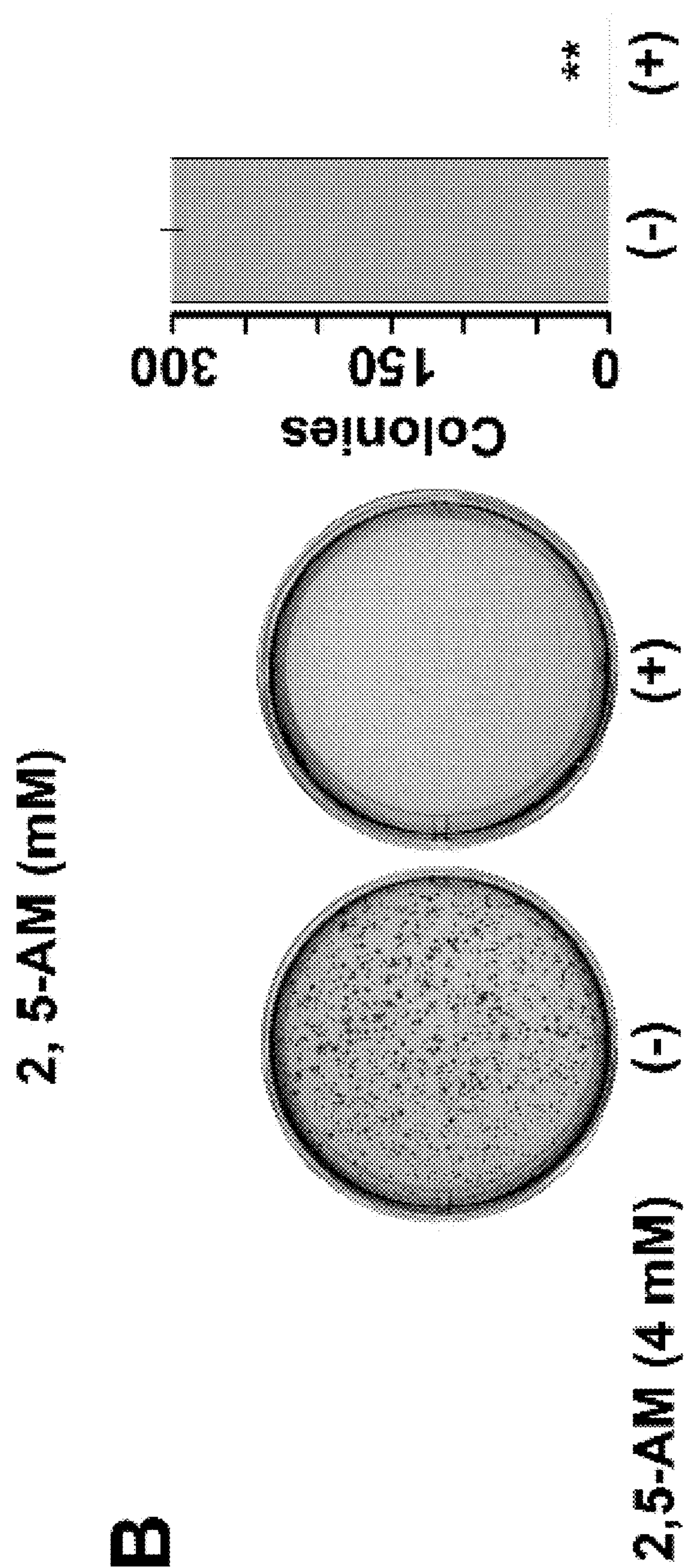
Figure 7C:
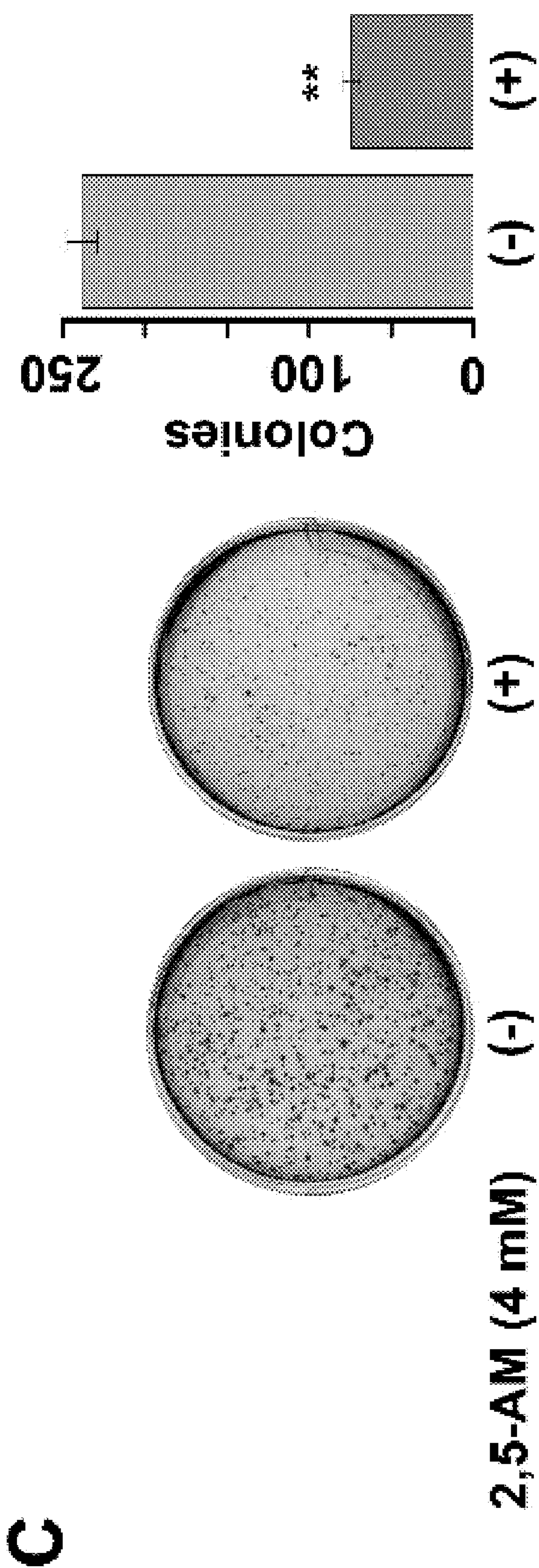
Figure 7D:
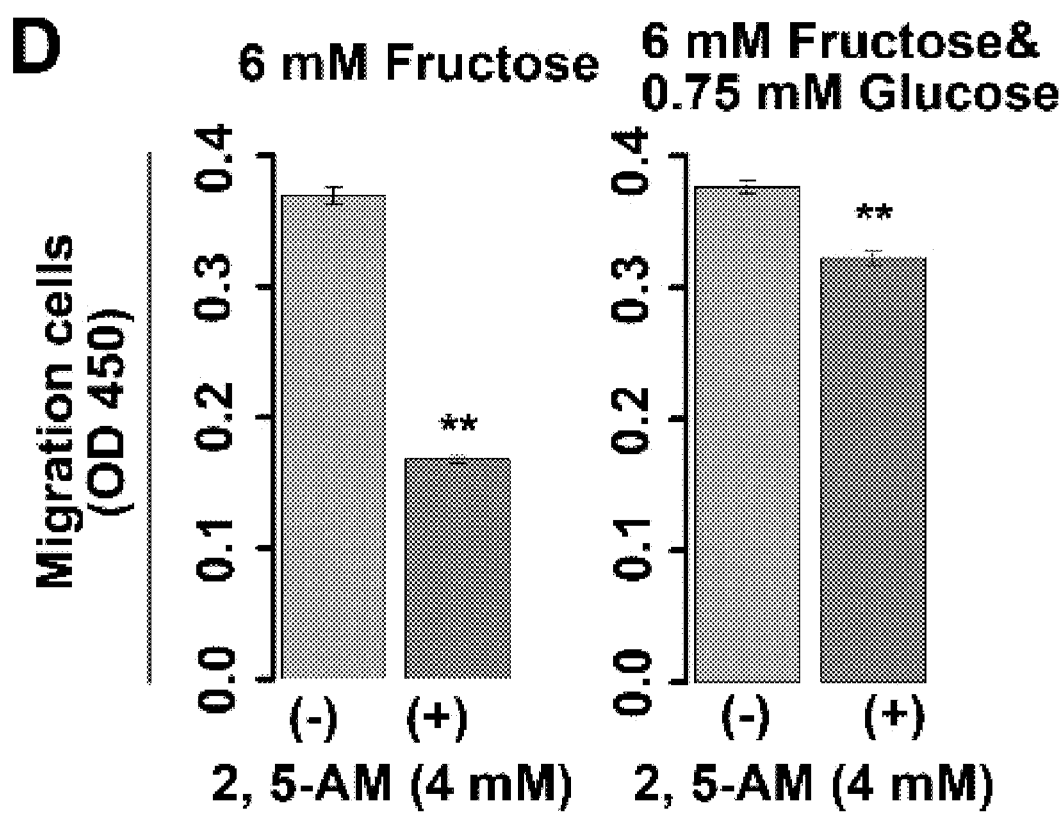
Figure 7E:
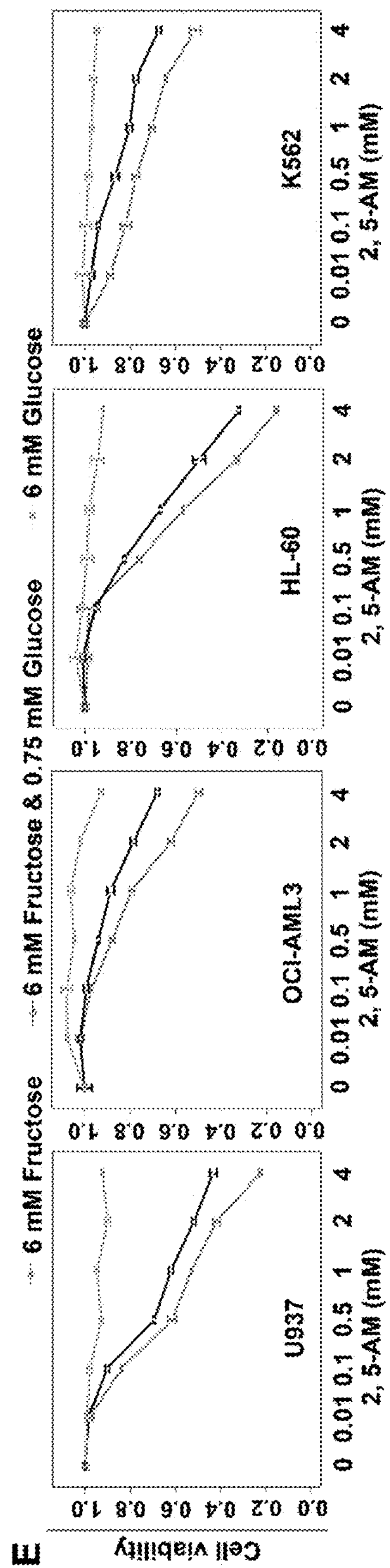
Figure 7F:
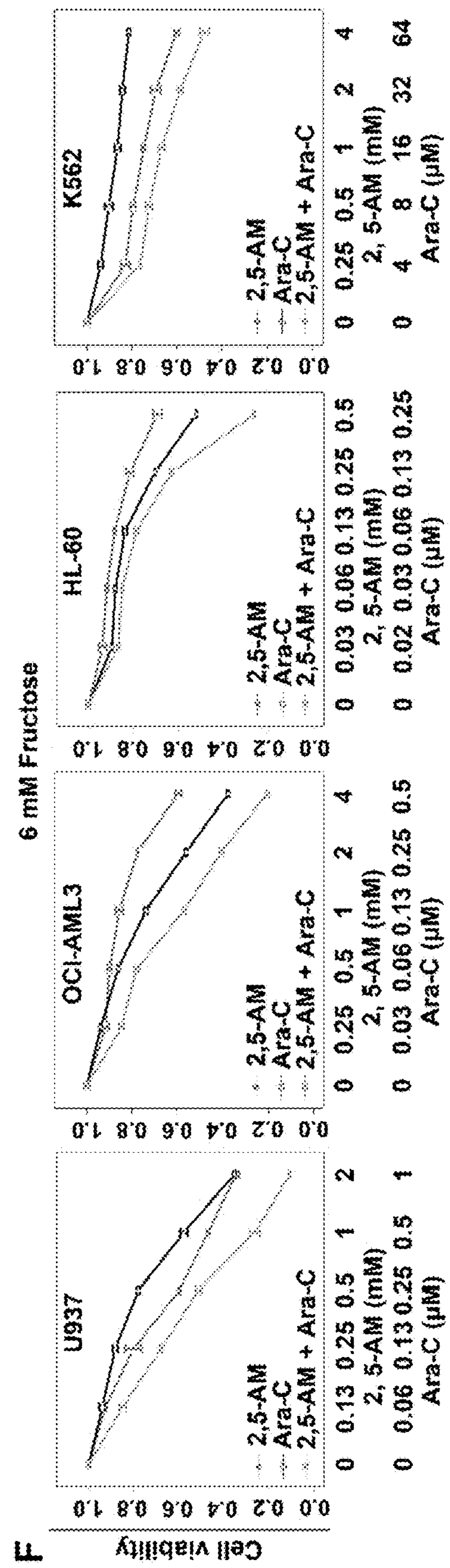
Figure 7G:
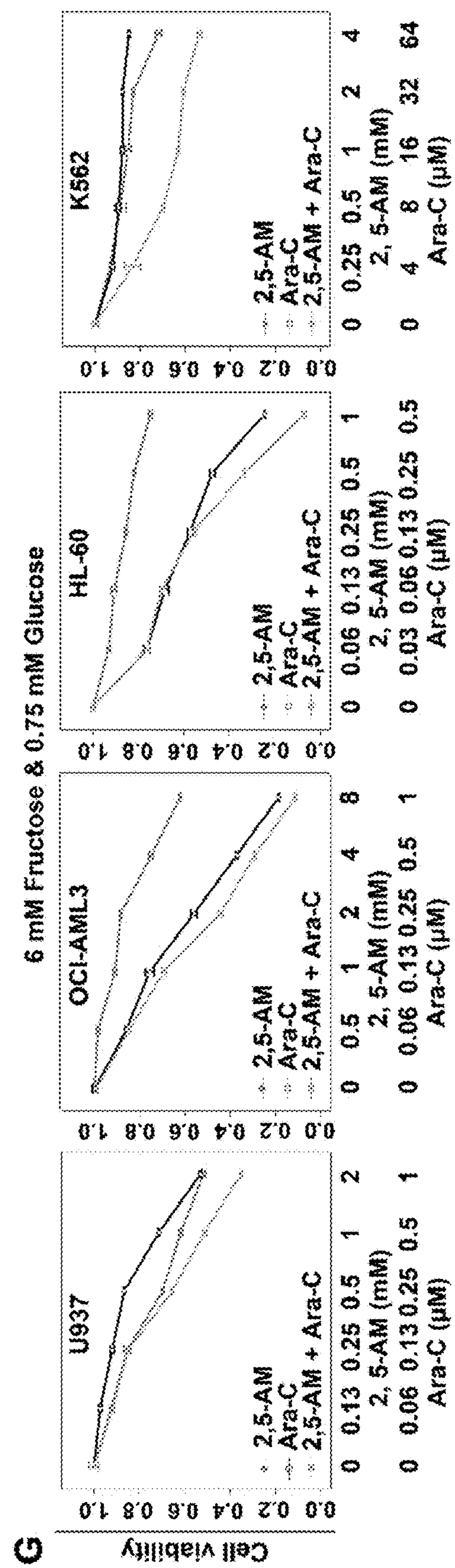
Figure 8A:
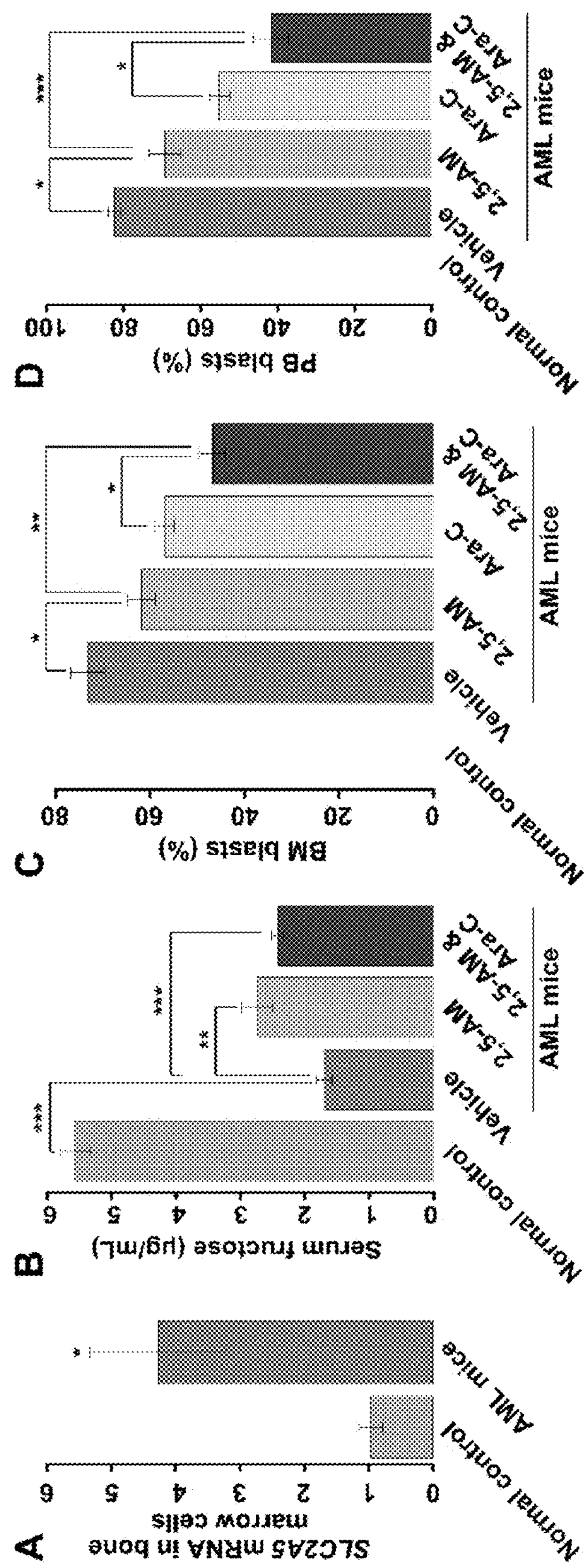
FIGS. 8A-8C. The use of 2,5-AM inhibited fructose utilization by AML mice, significantly alleviated leukemic phenotypes, and significantly enhanced therapeutic effects of Ara-C. Result A shows a higher level of SLC2A5 expression in bone marrow of AML mice compared to healthy controls; B shows the serum fructose concentrations for normal controls, AML mice treated with vehicle, AML mice treated with 2,5-AM, and AML mice treated with 2,5-AM and Ara-C. C shows the percentage of bone marrow blast cells in normal controls, AML mice treated with vehicle, AML mice treated with 2,5-AM, AML mice treated with Ara-C, and AML mice treated with 2,5-AM and Ara-C. D shows the percentage of PB blast cells in normal controls, AML mice treated with vehicle, AML mice treated with 2,5-AM, AML mice treated with Ara-C, and AML mice treated with 2,5-AM and Ara-C.
Figure 8B:
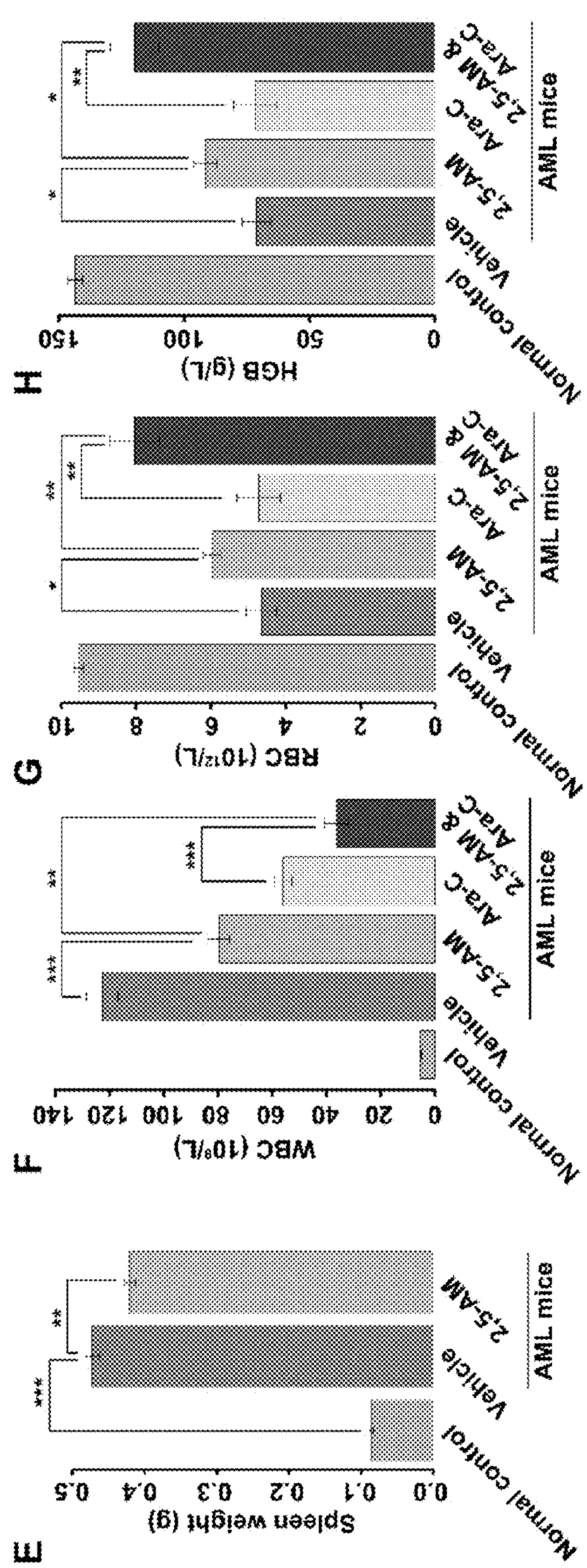
Figure 8C:
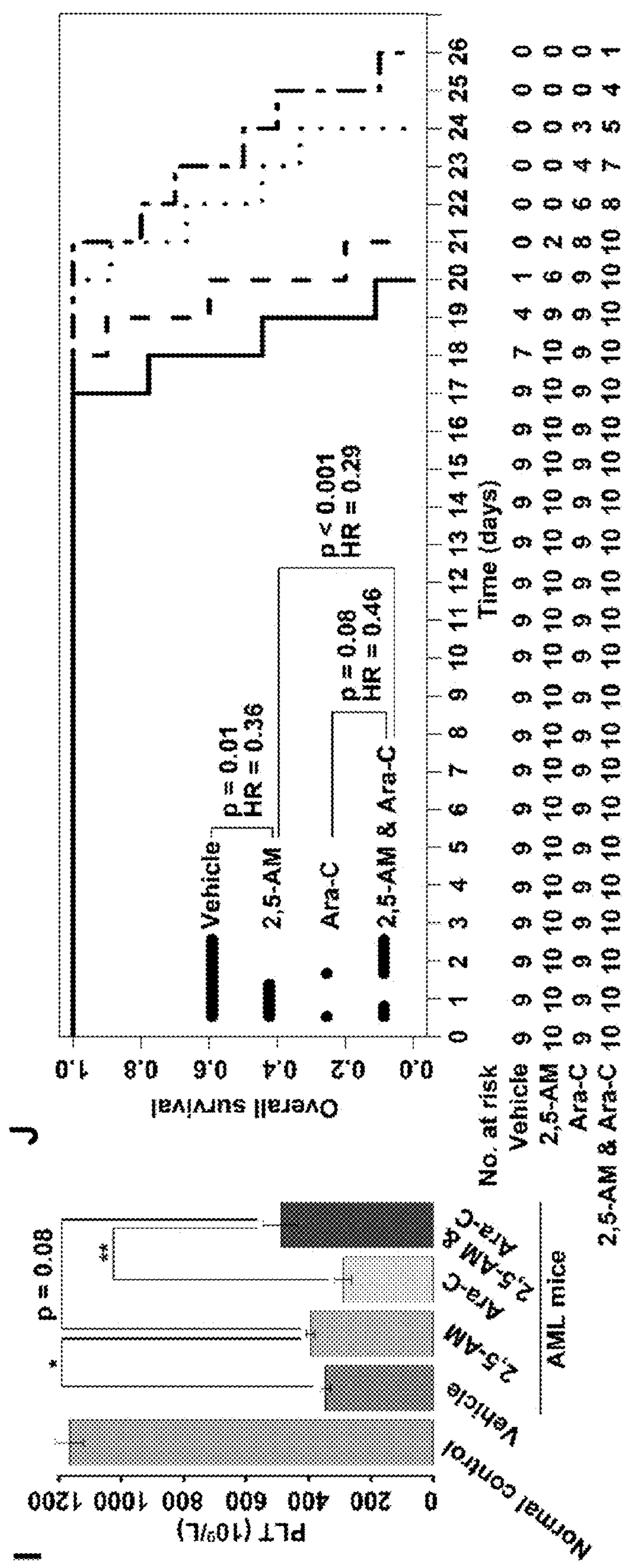

The inventors' previous studies have found that the higher the level of SLC2A5 expressed, or the higher the ability of fructose utilization, the worse the prognosis of the AML patients (FIG. 2A-2C). Enhanced fructose metabolism mediated by GLUTS exacerbates the malignant phenotype of AML cells, including increased cell proliferation, enhanced colony formation, and increased mobility and infiltration of AML cells (FIG. 3A-3D). In addition, the inventors have also found that cancerous tissues of pancreatic cancer patients expressed a higher level of fructose transporter gene SLC2A5 relative to adjacent non-cancerous tissues (FIGS. 4A-4D and FIGS. 5A and 5B), suggesting that pancreatic cancer cells are active in fructose transport and utilization. Further, the present inventors have found that fructose utilization mediated by GLUTS can significantly enhance the ability of pancreatic cancer cells to metastasize (FIG. 6A-6F). In vitro cell experiments showed that the use of fructose analog, 2,5-anhydro-D-mannitol (2,5-AM) blocked the fructose utilization in AML cells, significantly inhibited malignant cell proliferation, cell colony formation and cell migration (FIG. 7A-7G). Additionally 2,5-AM can kill AML cells in concert with conventional chemotherapeutic agents (FIG. 7A-7G). Mouse in vivo experiments showed that 2,5-AM significantly inhibited fructose utilization by AML cells improving the leukemic phenotype of AML mice and significantly prolonged the survival of AML mice (FIG. 8A-8C). It is worth noting that 2,5-AM and cytarabine had a good synergistic effect in AML mice (FIG. 8A-8C). In addition, the present inventors have found that the use of 2,5-AM to treat pancreatic cancer cells significantly inhibited fructose-induced malignant proliferation of pancreatic cancer cells (FIG. 9A-9C).

Based on the above evidence, the GLUTS-mediated fructose metabolism pathway is a new potential therapeutic target for cancer.

Application of Fructose Analogs 2,5-AM in the Treatment of AML and Pancreatic Cancer The present invention provides the use of fructose analogs such as 2,5-AM for the treatment of AML and pancreatic cancer, and uses the combination of 2,5-AM and conventional chemotherapeutic agents to further enhance the therapeutic effect. Conventional chemotherapeutic agents used in combination with 2,5-AM may include cytarabine (Ara-C), daunorubicin, doxorubicin, cisplatin, carboplatin, gemcitabine, capecitabine, sorafenib, docetaxel, paclitaxel, adriamycin, 5-fluorouracil, and so on. Other fructose analogs used in the methods of the present invention include analogs having the chemical structures shown in the present invention.

The Fructose Utilization by Other Solid Tumors, and the Use of Fructose Analog 2,5-AM to Treat these Tumors The present invention also examines the use of fructose in other solid tumor cells, including colorectal cancer cells, hepatocellular carcinoma cells and glioma cells, see FIG. 10A. The data show that colorectal cancer cells are very active in fructose utilization. A fructose analog, 2,5-AM, significantly inhibited fructose-induced colorectal cell proliferation (FIG. 10B and FIG. 10C). Other fructose analogs used in the methods of the present invention include analogs of the chemical structures shown in the present invention.

Fructose Analogue 2,5-AM Combined with Glucose Analogue 2-Deoxy-Glucose for the Treatment of Cancer The present inventors have also analyzed an anticancer effect in which both glucose utilization and fructose utilization are simultaneously inhibited. The present inventors have found that the combination of a glucose analogue 2-deoxy-glucose (2-DG) and 2,5-AM can kill AML cells more effectively (FIG. 11). Other fructose analogs and glucose analogs used in the methods of the present invention include analogs of the chemical structures shown in the present invention.

The Beneficial Effect of Present Invention

The present inventors first demonstrated that the GLUTS-mediated fructose metabolism plays an important role in the malignant progression of cancer through a large number of experiments and clinical data analyses. Second, the present inventors confirmed the apparent anti-cancer effect of the fructose analog, 2,5-AM, by in vitro cell models and in vivo experiments in cancer-bearing models, and confirmed that 2,5-AM can be used in combination with conventional chemotherapeutic agents to improve the treatment effect. The present invention provides new strategies and methods for improving the treatment of cancer.

The invention will now be further described with reference to specific embodiments. It is to be understood that these examples are merely illustrative of the invention and are not intended to limit the scope of the invention. The experimental methods specified in the following examples are generally carried out according to conventional conditions, such as those described in Sambrook et al., Molecular Cloning: Laboratory Manual (New York: Cold Spring Harbor Laboratory Press, 1989) or the conditions suggested by the vendors of the reagents.

Example 1. Fructose Analogue 2,5-AM Inhibits the Malignant Phenotype of AML Cells 2,5-AM significantly inhibited the malignant proliferation of AML cells U937-SLC2A5 (overexpressing the fructose transporter SLC2A5) in the culture conditions of 6 mM fructose or 6 mM fructose+0.75 mM glucose (FIG. 7A), colony formation (FIG. 7B) and cell migration (FIG. 7C). In addition, 2,5-AM significantly inhibited the malignant proliferation of four AML cells (U937, OCI-AML3, I-IL-60 and K562) under the culture conditions of 6 mM fructose or 6 mM fructose+0.75 mM glucose, but the cell proliferation under the 6 mM glucose condition was almost unaffected (FIG. 7E).

Example 2. Inhibitory Effect of Fructose Analogue 2,5-AM in Combination with Chemotherapeutic Drug, Cytarabine, on AML Cells In cell culture conditions with 6 mM fructose or 6 mM fructose+0.75 mM glucose, 2,5-AM could inhibit the proliferation of four AML cells, including U937, OCI-AML3, HL-60 and K562 cells.

Example 3. Effect of Fructose Analogue 2,5-AM on AML Model Mice

AML mice were generated using a previously reported procedure (Wang et al., 2011) with minor modifications. About $1\times10^5$ GFP-positive murine leukemic cells (splenic cells) with AML1-ETO and mutated C-KIT were injected into the tail vein of each sublethally irradiated (3.5 Gy), 8 week old BALB/c female mice. On day 5 after inoculation of AML cells, 2,5-AM was injected intraperitoneally at a dose of 150 mg/kg/day for continuous administration to mice. Control group AML mice were given saline injection according to the same dose and method. Compared with the control group, the bone marrow leukemia cells, peripheral blood leukemia cells and peripheral white blood cells of the 2,5-AM group were significantly inhibited, the spleen enlargement was significantly relieved, the peripheral blood red blood cell count, hemoglobin and platelet count were significantly increased (FIGS. 8A-8C, results C to I). In addition, the overall survival of mice in the 2,5-AM treatment group was significantly prolonged (FIG. 8C, result J).

Example 4. Effect of Fructose Analogue 2,5-AM in Combination with chemotherapeutic drug cytarabine on the treatment of AML model mice (Ara-C) was administered intraperitoneally at a dose of 25 mg/kg/day on the third day in the AML model mice (see example 3) for 3 days after AML cell inoculation. At the same time, mice were intraperitoneally injected with 2,5 AM at a dose of 150 mg/kg/day on day 5 after AML cell inoculation, until mice were dead. (2) Ara-C alone group: In the AML model mice of Example 3, Ara-C was injected intraperitoneally at a dose of 25 mg/kg/day on the third day after AML cell inoculation for 3 days. Compared with the single 2,5-AM group and the single Ara-C group, the myeloid leukemia cells, peripheral blood leukemia cells and peripheral white blood cells of the 2,5-AM and Ara-C combination group were further inhibited, and the peripheral blood, the red blood cell count, hemoglobin and platelet count were further upregulated, and the overall survival of the mice was further prolonged (FIGS. 8A-8C, results C-J).

Example 5. Inhibitory Effect of Fructose Analogue 2,5-AM on Pancreatic Cancer Cells The proliferation of PANC-1, CFPAC-1 and BxPC-3 was significantly inhibited by 2,5-AM in 6 mM fructose culture (FIGS. 9A-9C).

Example 6. Inhibitory Effect of Fructose Analogs 2,5-AM on Other Solid Tumor Cells In 6 mM fructose culture, 2,5-AM significantly inhibited the malignant proliferation of colorectal cancer cells HCT-15 and HCT-116 (FIGS. 10A-10C).

Example 7 Anti-Cancer Effect of Fructose Analogue 2,5-AM and Glucose Analogue 2-Deoxy-Glucose (2-DG)

The combination of 2,5-AM and 2-DG was able to synergistically kill AML cells, including U937 and HL-60 (FIG. 11), in 6-mg fructose+0.75 mM glucose culture.

All documents mentioned in the present invention are hereby incorporated by reference as if each of the documents was individually cited for reference. It is to be understood that various changes and modifications may be made by those skilled in the art upon reading the above teachings of the present invention, which also fall within the scope of the claims appended hereto.

The invention claimed is:

1. A method of treating a cancer selected from acute myeloid leukemia, pancreatic cancer, and lung cancer, the method comprising administering to a subject in need thereof a fructose analog selected from the group consisting of:

2,5-anhydro-D-mannitol;

a 2,5-anhydro-D-mannitol derivative substituted at the 1-position or 6-position by an amino group, an alkyl group or an aryl group;

2,5-anhydro-D-mannitol tetraacetate; and 2,5-anhydroglucitol.

2. A method of treating cancer comprising administering to a subject in need thereof a fructose analog selected from the group consisting of:

2,5-anhydro-D-mannitol;

a 2,5-anhydro-D-mannitol derivative substituted at the 1-position or 6-position by an amino group, an alkyl group or an aryl group;

2,5-anhydro-D-mannitol tetraacetate; and 2,5-anhydroglucitol, wherein the cancer is selected from acute myeloid leukemia, pancreatic cancer, colorectal cancer and lung cancer.

3. A method of treating a cancer selected from acute myeloid leukemia (AMU), pancreatic cancer, lung cancer, and colorectal cancer comprising administering to a subject in need thereof a fructose analog and an anticancer agent, wherein the fructose analog is selected from the group consisting of:

2,5-anhydro-D-mannitol;

a 2,5-anhydro-D-mannitol derivative substituted at the 1-position or 6-position by an amino group, an alkyl group or an aryl group;

2,5-anhydro-D-mannitol tetraacetate; and 2,5-anhydroglucitol; and the anticancer agent is selected from the group consisting of cytarabine (Ara-C), daunorubicin, doxorubicin, cisplatin, carboplatin, gemcitabine, capecitabine, sorafenib, docetaxel, paclitaxel, adriamycin, and 5-fluorouracil.

* * * * *